United States Patent
Yi et al.

(10) Patent No.: US 11,185,568 B2
(45) Date of Patent: Nov. 30, 2021

(54) METHODS FOR GENERATION OF CELL-DERIVED MICROFILAMENT NETWORK

(71) Applicant: President and Fellows of Harvard College, Cambridge, MA (US)

(72) Inventors: Tingfang Yi, Chestnut Hill, MA (US); Gerhard Wagner, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/074,539

(22) PCT Filed: Apr. 13, 2018

(86) PCT No.: PCT/US2018/027583
§ 371 (c)(1),
(2) Date: Aug. 1, 2018

(87) PCT Pub. No.: WO2018/191672
PCT Pub. Date: Oct. 18, 2018

(65) Prior Publication Data
US 2020/0138904 A1    May 7, 2020

Related U.S. Application Data

(60) Provisional application No. 62/485,422, filed on Apr. 14, 2017.

(51) Int. Cl.
| | |
|---|---|
| *C12N 5/00* | (2006.01) |
| *C12N 5/071* | (2010.01) |
| *C12N 5/095* | (2010.01) |
| *A61K 38/17* | (2006.01) |
| *A61K 9/70* | (2006.01) |
| *A61K 35/36* | (2015.01) |
| *A61L 27/36* | (2006.01) |
| *A61L 27/54* | (2006.01) |
| *A61L 27/56* | (2006.01) |
| *A61L 27/58* | (2006.01) |
| *A61L 27/60* | (2006.01) |

(52) U.S. Cl.
CPC ............ *A61K 38/1719* (2013.01); *A61K 9/70* (2013.01); *A61K 35/36* (2013.01); *A61L 27/36* (2013.01); *A61L 27/54* (2013.01); *A61L 27/56* (2013.01); *A61L 27/58* (2013.01); *A61L 27/60* (2013.01)

(58) Field of Classification Search
None
See application file for complete search history.

(56) References Cited

U.S. PATENT DOCUMENTS

| | | |
|---|---|---|
| 4,123,610 A | 10/1978 | Summerton et al. |
| 4,981,985 A | 1/1991 | Kaplan et al. |
| 5,563,056 A | 10/1996 | Swan et al. |
| 5,830,708 A | 11/1998 | Naughton |
| 7,323,305 B2 | 1/2008 | Leamon et al. |
| 7,473,767 B2 | 1/2009 | Dimitrov |
| 8,551,710 B2 | 10/2013 | Bernitz et al. |
| 9,217,151 B2 | 12/2015 | Yin et al. |
| 2002/0015952 A1 | 2/2002 | Anderson et al. |
| 2002/0155989 A1 | 10/2002 | Efimov et al. |
| 2003/0148335 A1 | 8/2003 | Shen et al. |
| 2004/0077014 A1 | 4/2004 | Becker |
| 2004/0248144 A1 | 12/2004 | Mir |
| 2004/0259190 A1 | 12/2004 | Naughton |
| 2005/0106629 A1 | 5/2005 | McGrath et al. |
| 2005/0147981 A1 | 7/2005 | Yamakawa et al. |
| 2005/0233318 A1 | 10/2005 | Chee et al. |
| 2006/0024711 A1 | 2/2006 | Lapidus et al. |
| 2006/0177833 A1 | 8/2006 | Brenner |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |

(Continued)

FOREIGN PATENT DOCUMENTS

| | | |
|---|---|---|
| KR | 20080003402 A | 1/2008 |
| WO | 9746704 A1 | 12/1997 |

(Continued)

OTHER PUBLICATIONS

Mandal et al ., Biospinning by silkworms: Silk fiber matrices fortissue engineering applications Acta Biomaterialia 6 (2010) 360-371.*
Yi et al 4EGI-1 targets breast cancer stem cells by selective inhibition of translation that persists in CSC maintenance, proliferation and metastasis Oncotarget, vol. 5, No. 15 Jun. 18, 2014 pp. 6028-6037.*
Gomm et al (Journal of Cellular Physiology 171:11-19 (1997) Separated Human Breast Epithelial and Myoepithelial Cells Have Different Growth Factor Requirements In Vitro But Can Reconstitute Normal Breast Lobuloalveolar Structure.*

(Continued)

*Primary Examiner* — Maria G Leavitt
(74) *Attorney, Agent, or Firm* — Banner & Witcoff, Ltd.

(57) ABSTRACT

This invention provides for a network of cell-derived microfilaments. Also provided are methods of producing a network of microfilaments via culturing cells in a matrix support and cell culture medium wherein the cells proliferate and form aggregated cell masses, which produce microfilaments external to and surrounding the cell masses, and wherein the extracellular microfilaments connect and form a continuous extracellular microfilament network, and methods for treating a medical condition as well as facilitating wound repair and tissue regeneration comprising applying the microfilament network to an area in need of treatment.

17 Claims, 15 Drawing Sheets

(56) References Cited

U.S. PATENT DOCUMENTS

| | | |
|---|---|---|
| 2008/0176769 A1 | 7/2008 | Rank et al. |
| 2009/0005259 A1 | 1/2009 | Drmanac |
| 2009/0208965 A1 | 8/2009 | Tafas et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0086774 A1 | 4/2011 | Dunaway |
| 2011/0092376 A1 | 4/2011 | Colston, Jr. et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2013/0017229 A1 | 1/2013 | Mooney et al. |
| 2013/0245096 A1 | 9/2013 | Abitbol |
| 2014/0087378 A1 | 3/2014 | Chatre et al. |
| 2014/0220587 A1 | 8/2014 | Green, Jr. et al. |
| 2015/0133319 A1 | 5/2015 | Fu et al. |
| 2016/0024555 A1 | 1/2016 | Church et al. |
| 2016/0265046 A1 | 9/2016 | Zhang et al. |
| 2017/0212983 A1 | 7/2017 | Cai et al. |

FOREIGN PATENT DOCUMENTS

| | | | |
|---|---|---|---|
| WO | 01/26708 A1 | 4/2001 | |
| WO | 2004/046337 A2 | 6/2004 | |
| WO | 2007086900 A2 | 8/2007 | |
| WO | 2007/121489 A2 | 10/2007 | |
| WO | 2008069973 A2 | 6/2008 | |
| WO | 2009046149 A1 | 4/2009 | |
| WO | 2010080134 A1 | 7/2010 | |
| WO | 2011/143583 A1 | 11/2011 | |
| WO | 2012005595 A2 | 1/2012 | |
| WO | 2012/058638 A2 | 5/2012 | |
| WO | 2012150035 A1 | 11/2012 | |
| WO | 2013/055995 A2 | 4/2013 | |
| WO | 2014/163886 A1 | 10/2014 | |
| WO | 2014/182528 A2 | 11/2014 | |
| WO | 2015/118029 A1 | 8/2015 | |
| WO | 2016/192571 A1 | 12/2016 | |

OTHER PUBLICATIONS

Li et al Three-dimensional co-culture of BM-MSCs and eccrine sweat gland cells in Matrigel promotes transdifferentiation of BM-MSCs Journal of Molecular Histology vol. 46, pp. 431-438(2015).*

Corning® Matrigel® Matrix (pp. 1-6; down loaded on Jan. 8, 2021.*

Jayatilaka et al., Synergistic IL-6 and IL-8 paracrine signalling pathway infers a strategy to inhibit tumour cell migration Nature Communications pp. 1-12.*

Lee et al., Three-dimensional culture models of normal and malignant breast epithelial cells 2007, Nature Methods 359-365.*

Almeida et al., Influence of a reconstituted basement membrane and its components on casein gene expression and secretion in mouse mammary epithelial cells, 1996 J Dairy Sci 79:1021-1026.*

Dec. 18, 2014 (PCT) International Preliminary Report—App PCT/US2013/044241.

Ascano, M et al. Identification Of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Cao, Yi et al.,"In-situ immuno-PCR to detect antigens," The Lancet, Sep. 16, 2000, pp. 1002-1003, vol. 356.

Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retrieved from the Internet: URL:http://dspace.mit.edu/bitstream/handle/1721.1/107103/971494098-MIT.pdf?sequence=1 [retrieved on Feb. 20, 2019].

Eliscovich et al. mRNAon the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.

Extended European Search Report dated May 13, 2019 for EP Application No. 16862929.3.

Extended European Search Report dated May 21, 2019 for European Application No. 16862945.9.

Ginart, P et al. RNA Sequencing In Situ. Nat Biotechnol. Jun. 2014, vol. 32, No. 6; pp. 543-544; DOI: 10.1038/nbt.2921.

Grompe (1993) Nature Genetics DOI: 10.1038/ng1093-111.

Han et al. "Quantum-dot-tagged microbeads for multiplexed optical coding of biomolecules". Nature Biotechnology, vol. 19, 99 631-635 (Jul. 31, 2001).

International Search Report and Written Opinion based on PCT/US2018/027583 dated Jun. 29, 2018.

International Search Report and Written Opinion issued in corresponding International Application No. PCT/US2012/071398, dated Apr. 8, 2013.

Jambhekar et al. Cis-acting determinants of asymmetric, cytoplasmic RNA transport. RNA, vol. 13, pp. 625-642, 2007 (Year: 2007).

Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.

Lee, JH et al. Highly Multiplexed Subcellular RNA Sequencing In Situ. Science. Mar. 21, 2014, vol. 343, No. 6177, pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Matlin et al. Spatial expression of the genome: the signal hypothesis at forty. Nature Reviews. Molecular Cell Biology, vol. 12, No. 5, pp. 333-340, May 2011, Epub Apr. 2011 (Year: 2011).

Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).

Office Action issued for corresponding European Patent Application No. 12780609.9, dated Sep. 23, 2015.

Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).

Saliba, AE et al. Single-Cell RNA-Seq: Advances And Future Challenges. Nucleic Acids Res. Jul. 22, 2014, vol. 42, No. 14; pp. 8845-8860; DOI: 10.1093/nar/gku555.

Sano, Takeshi et al. "Immuno-PCR: Very Sensitive Antigen Detection by Means of Specific Antibody-DNA Conjugates," Science, Oct. 2, 1992, pp. 120-122, vol. 258.

Schweitzer, Barry et al., "Immunoassays with rolling circle DNA amplification: A versatile platform for ultrasensitive antigen detection" PNAS, Aug. 29, 2000, p. 10113-10119, vol. 97, No. 18.

Seo, et al. Four-color DNA sequencing by synthesis on a chip using photocleavable fluorescent nucleotides. Proceeding of the National Academy of Sciences, Apr. 2005, 102 (17) 5926-5931.

Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.

(56) References Cited

OTHER PUBLICATIONS

Singer-Kruger et al. Here, there, everywhere. RNA Biology, vol. 11, No. 8, pp. 1031-1039, Aug. 2014. (Year 2014).
Soderberg, Ola et al.,"Direct observation of individual endogenous protein complexes in situ by proximity ligation," Nature Methods, Dec. 2006, pp. 995-1000, vol. 3, No. 12, Nature Publishing Group.
Thisse et al. "High-Resolution in situ hybridization to whole-mount zebrafish embryos" 2008. Nature Protocols. vol. 3 No. 1 pp. 59-69. Doi:10 1038/nprot.2007.514.
Thisse et al. 2008 Nature protocols vol. 3 No 1 pp. 59-69. Doi:10. 1038/nprot.2007.514.
Tsaftaris et al. Isolation of three homologous AP1-like MADS-box genes in crocus (*Crocus sativus* L.) and characterization of their expression. Plant Science, vol. 166, No. 5, pp. 1235-1243, May 2004 (Year 2004).
Weis et al. Protein targeting to subcellular organelles via mRNA localization. Biochimica et Biophysica Acta, vol. 1833, pp. 260-273, 2013, available online Apr. 2012 (Year 2012).
Vogel et al., "Myosin motors fragment and compact membrane-bound actin filaments," ELIFE, vol. 2 (Jan. 8, 2013).
Gardel et al., "Elastic Behavior of Cross-Linked and Bundled Actin Networks," The 3rd EAA European Congress on Acoustics (Forum Acusticum 2002), vol. 304, No. 5675, pp. 1301-1305 (May 28, 2004).
Yi et al., "Cytocapsular tubes conduct cell translocation," Proceedings of the National Academy of Sciences, vol. 115, No. 6, pp. E1137-E1146 (Jan. 16, 2018).
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
Choi, Harry M.T et al., "Next-Generation in Situ Hybridization Chain Reaction: Higher Gain, Lower Cost, Greater Durability" ACS NANO, vol. 8, No. 5, May 27, 2014 (May 27, 2014), pp. 4284-4294, XP055409053, US.
Extended European Search Report issued for EP Application No. 17790240.0 dated Sep. 4, 2019.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.

\* cited by examiner

FIG. 1A-F
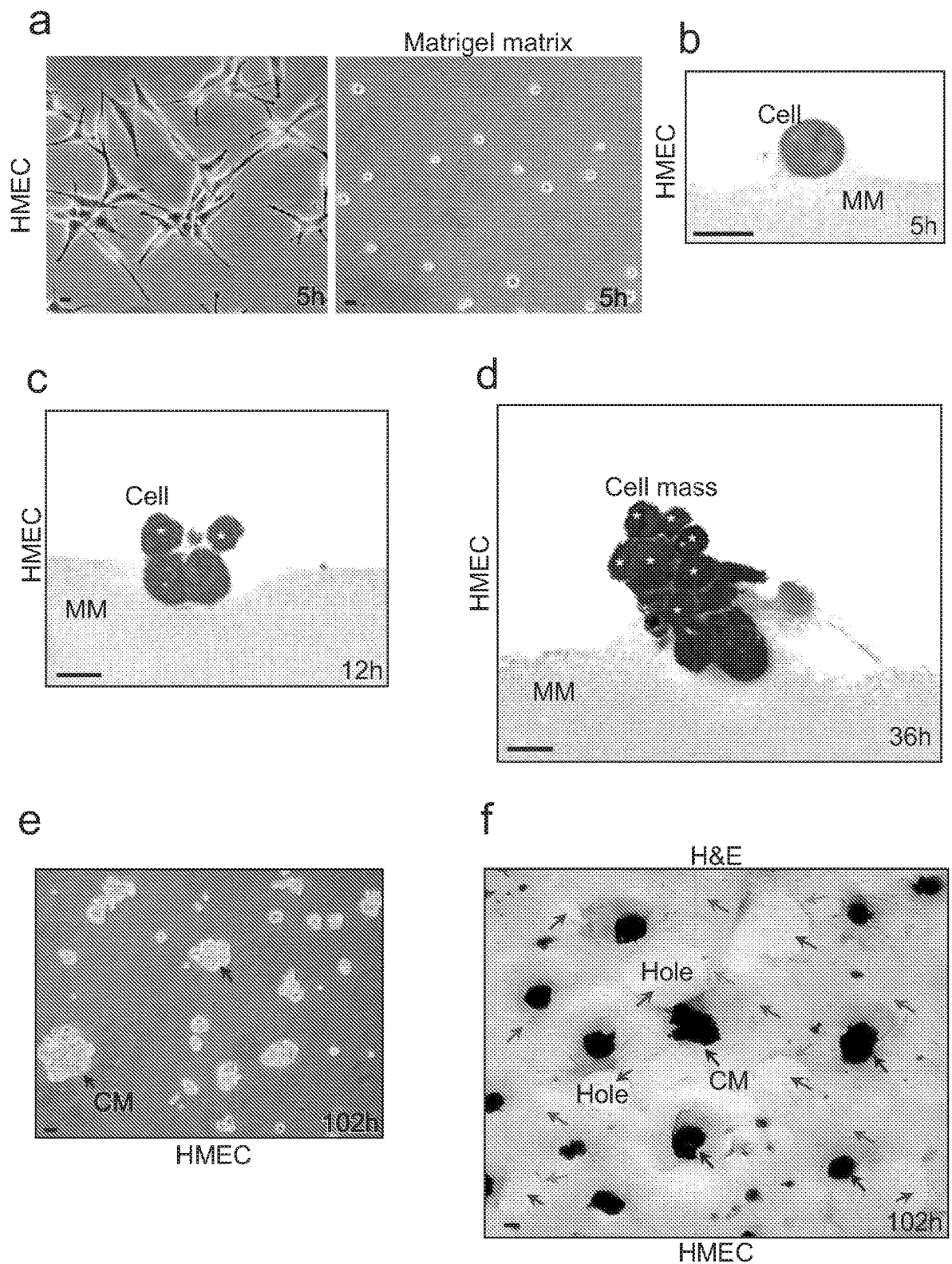

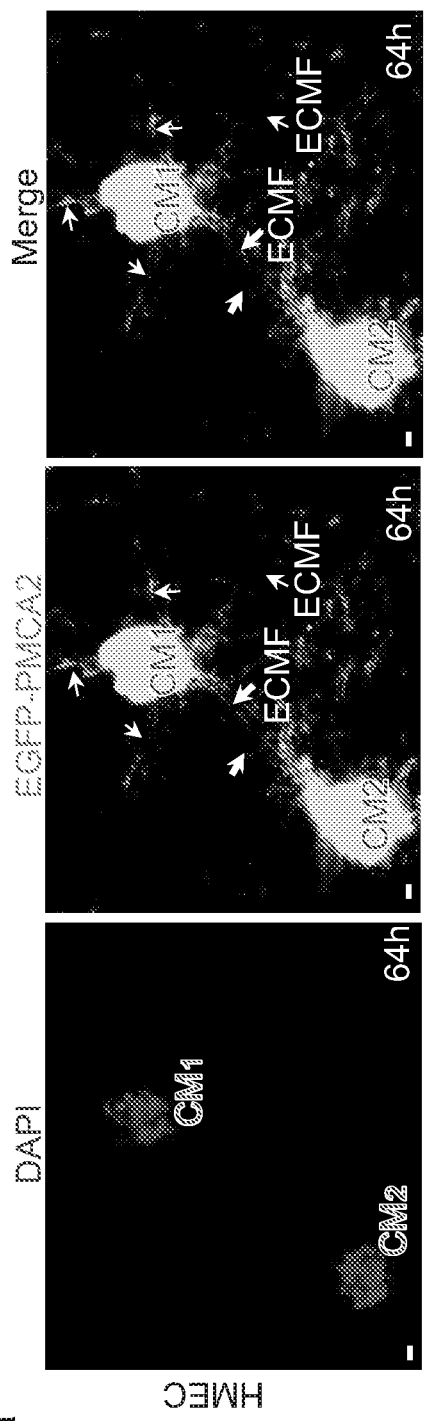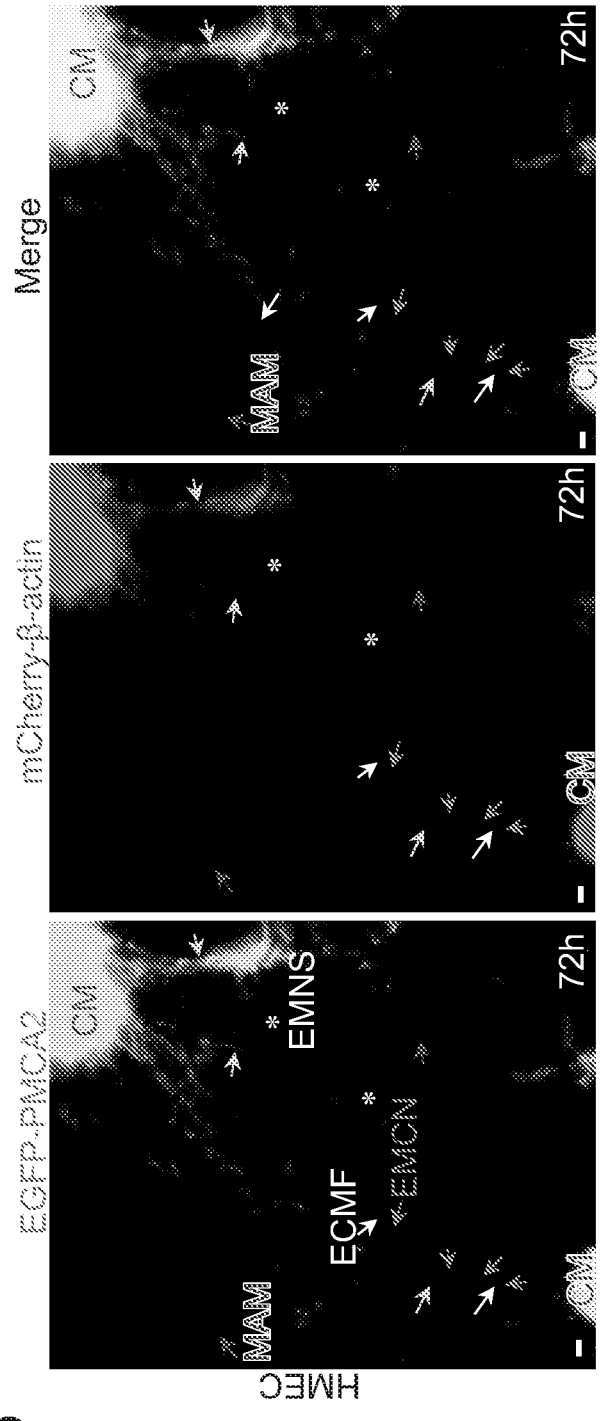
FIG. 2A-B

FIG. 8A-C
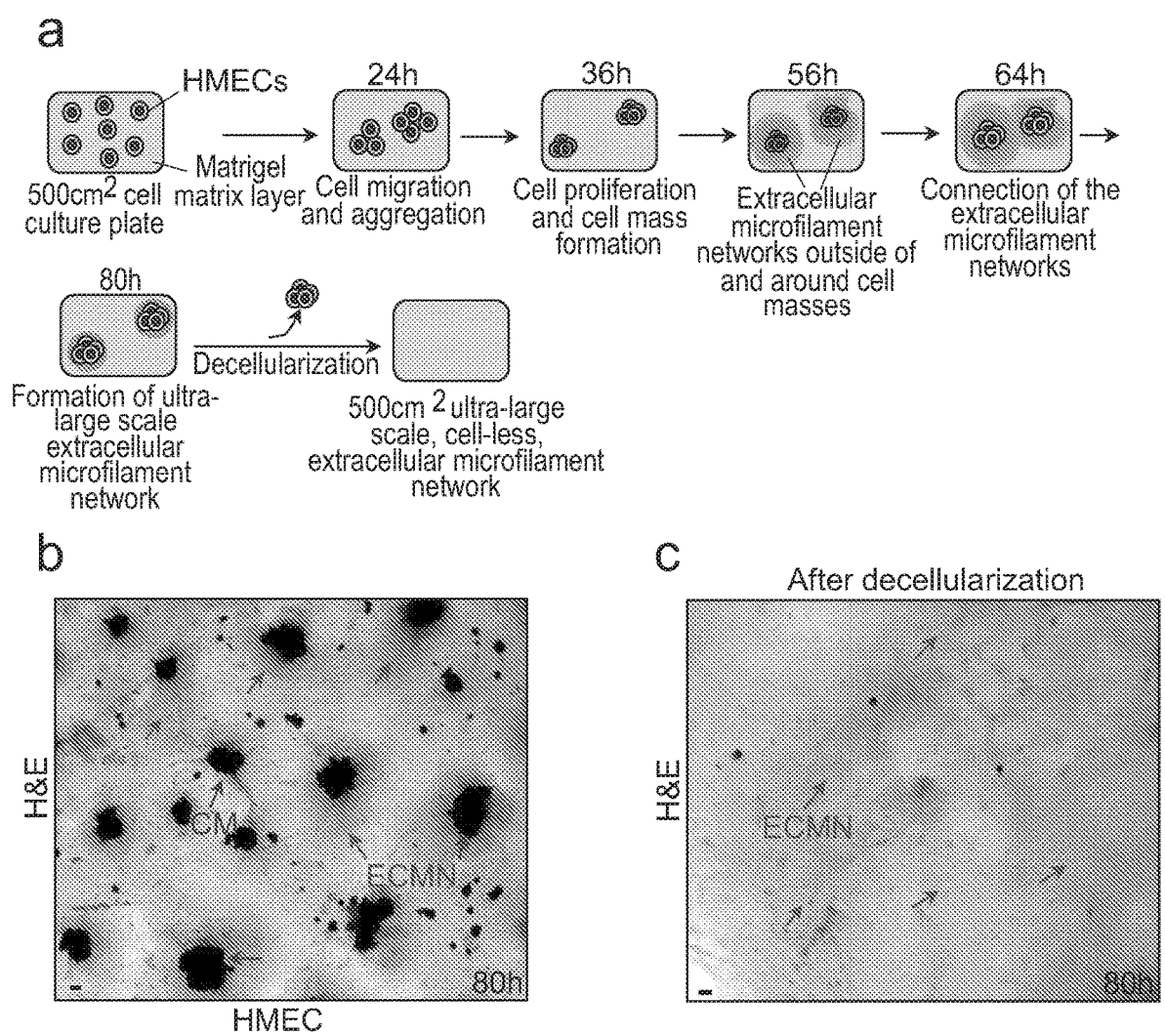

FIG. 9A-D
a
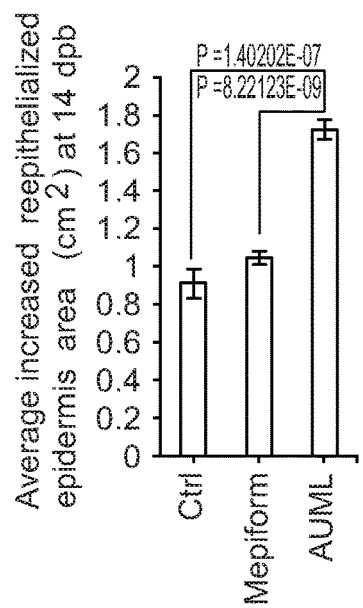
b
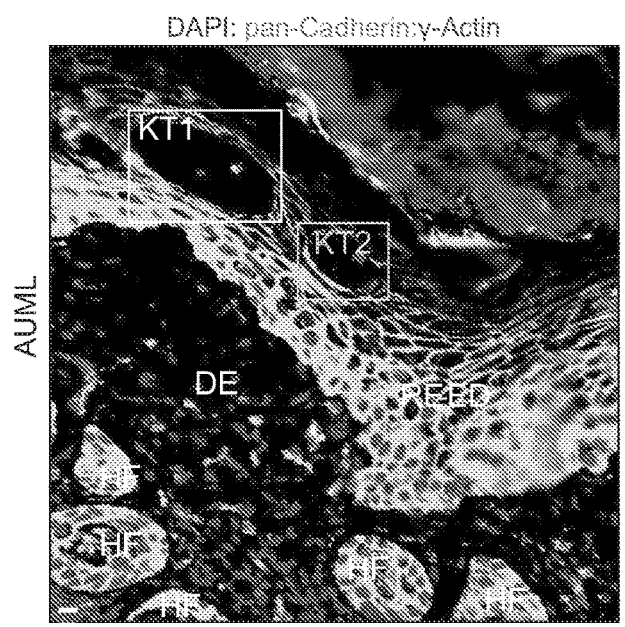
c
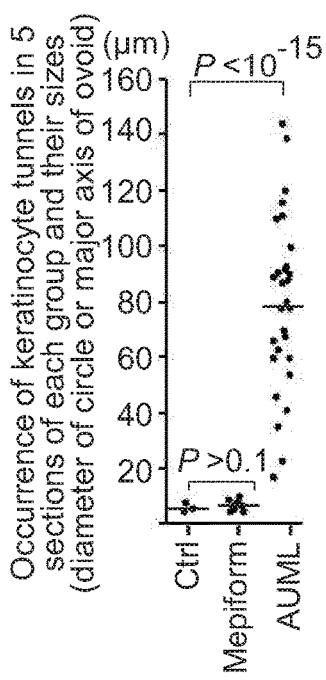
d
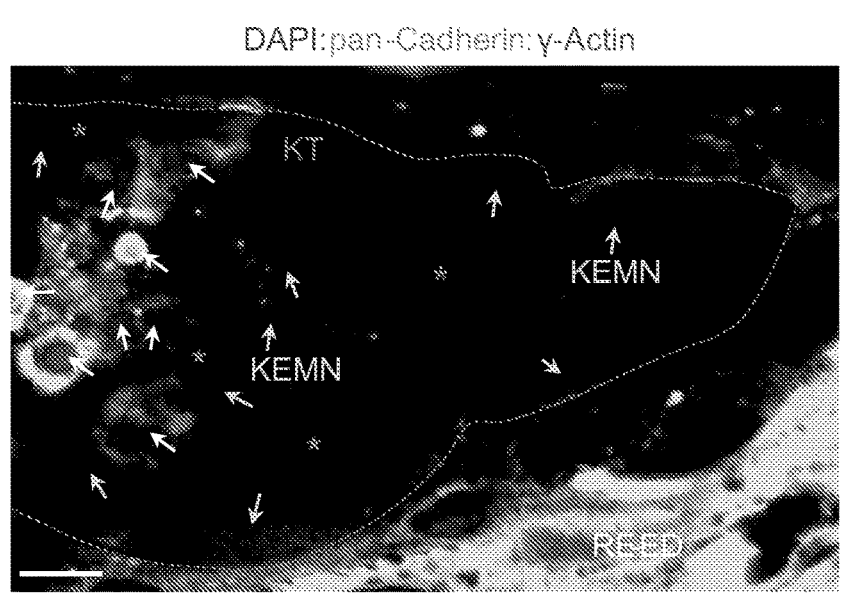

FIG. 10A-B
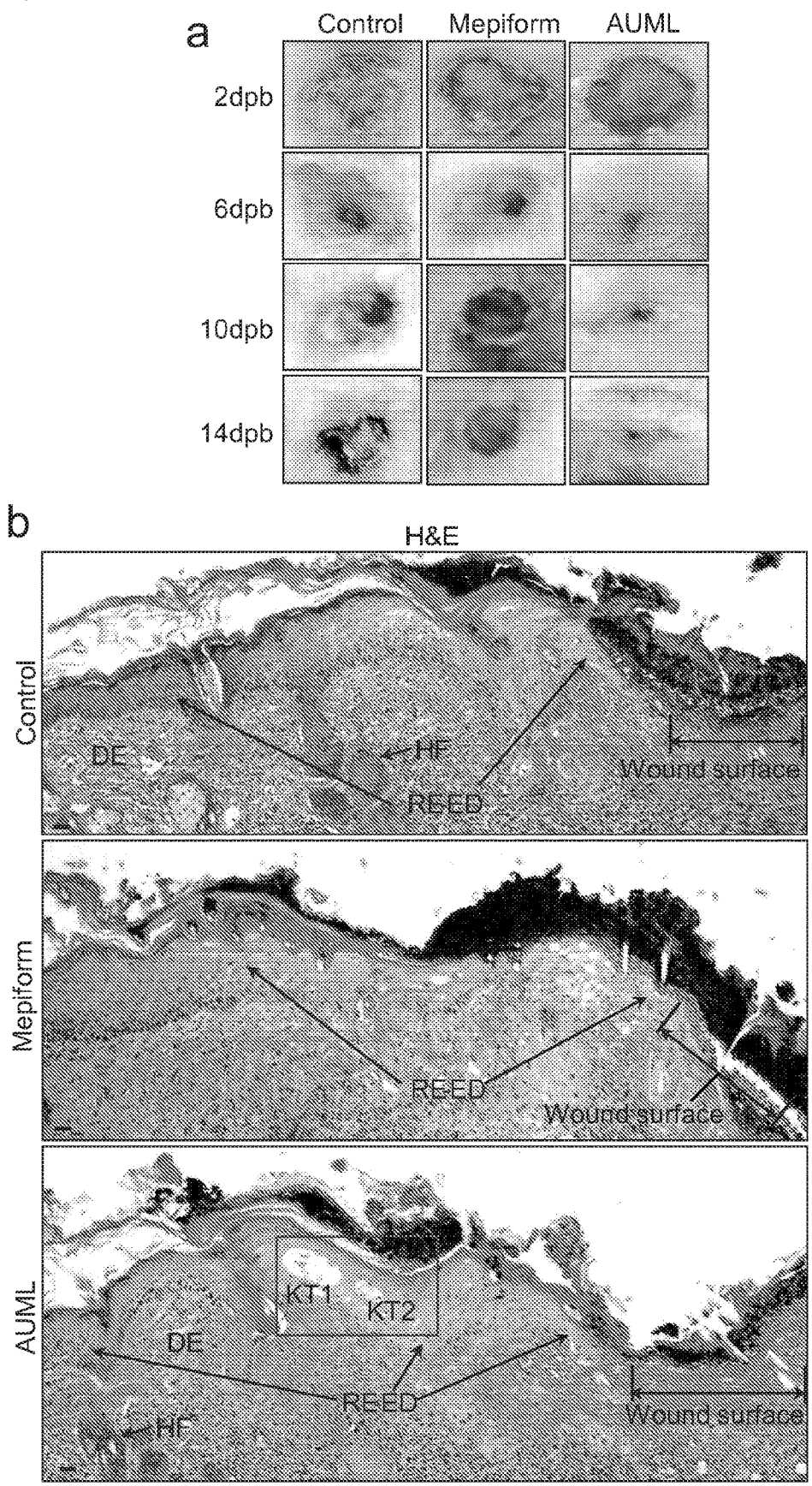

FIG. 11A-C
a
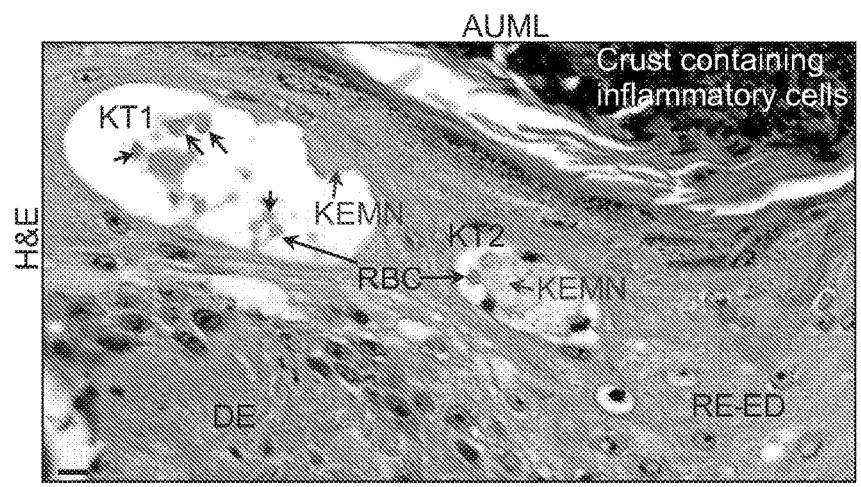
b
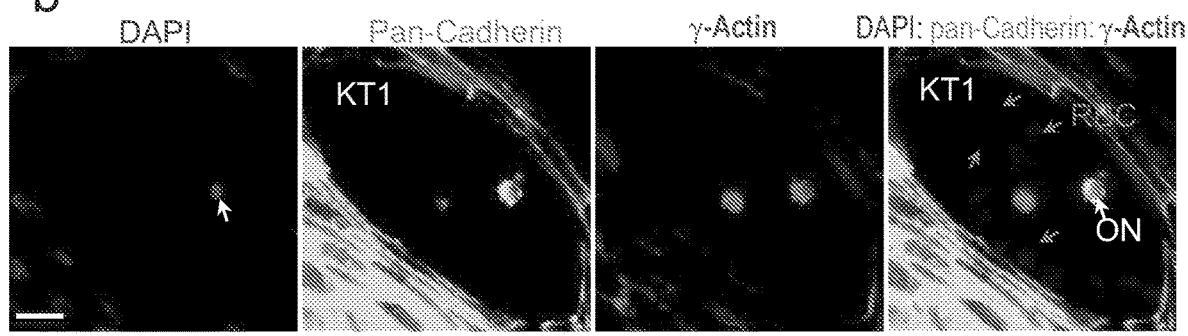
c
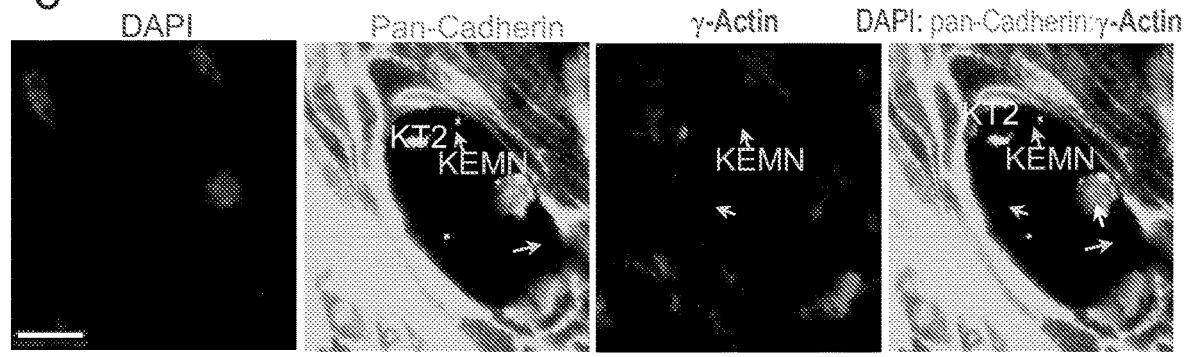

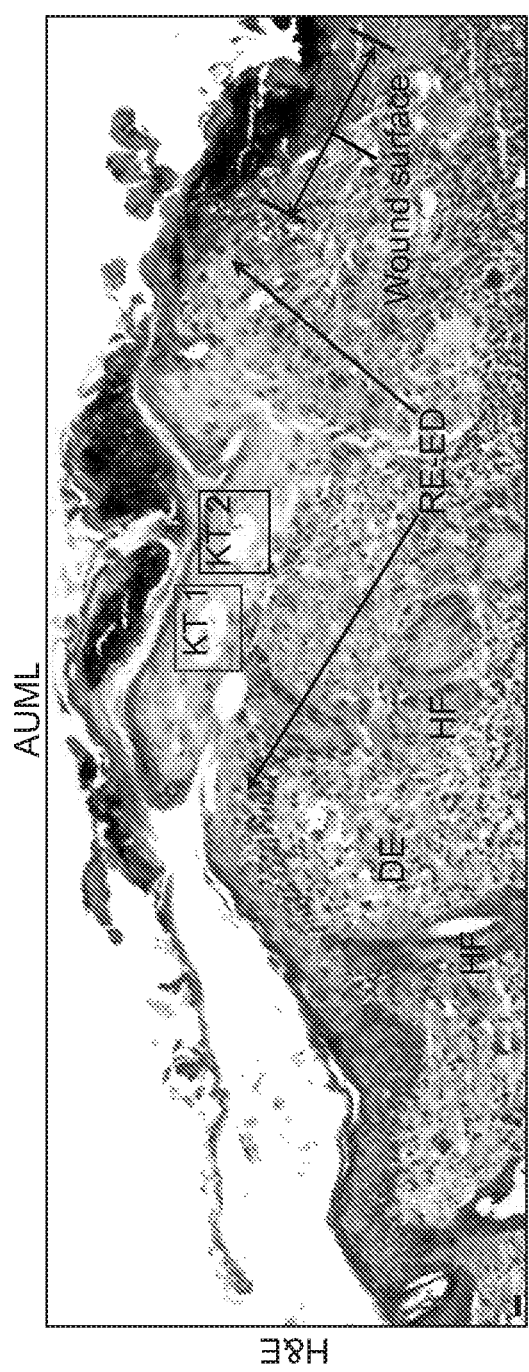
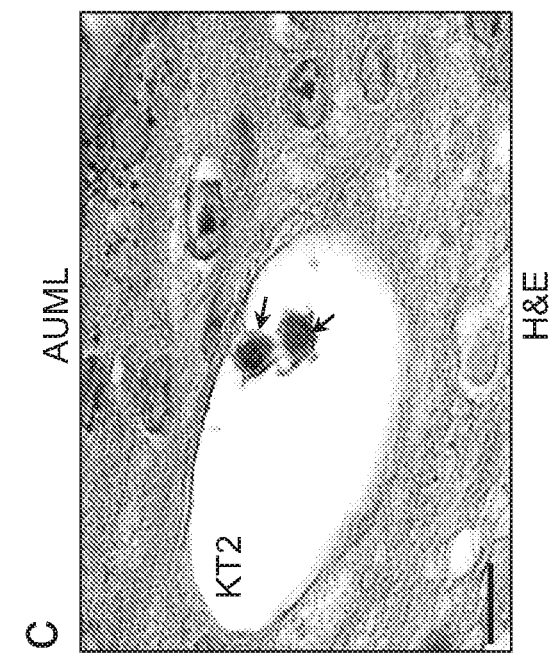
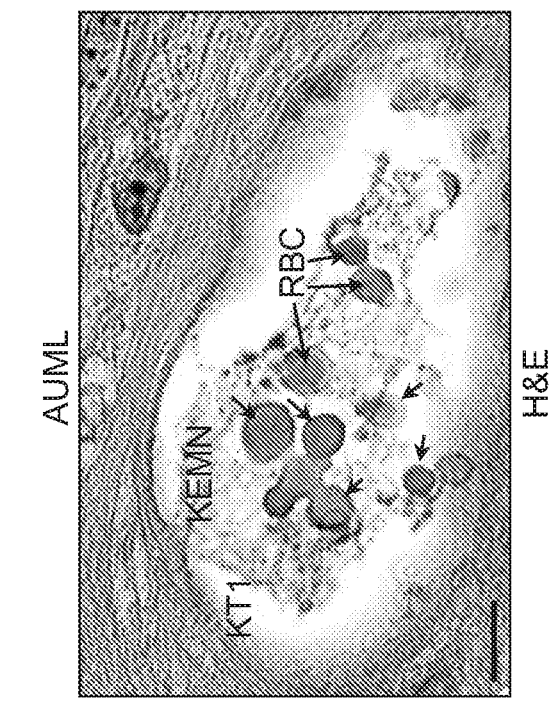
FIG. 12A-C

FIG. 13A-C
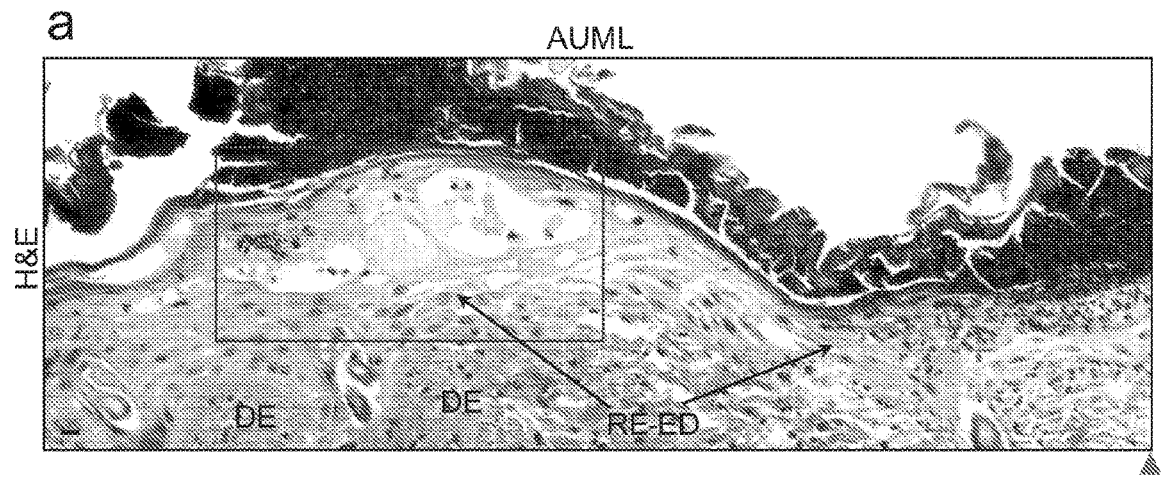
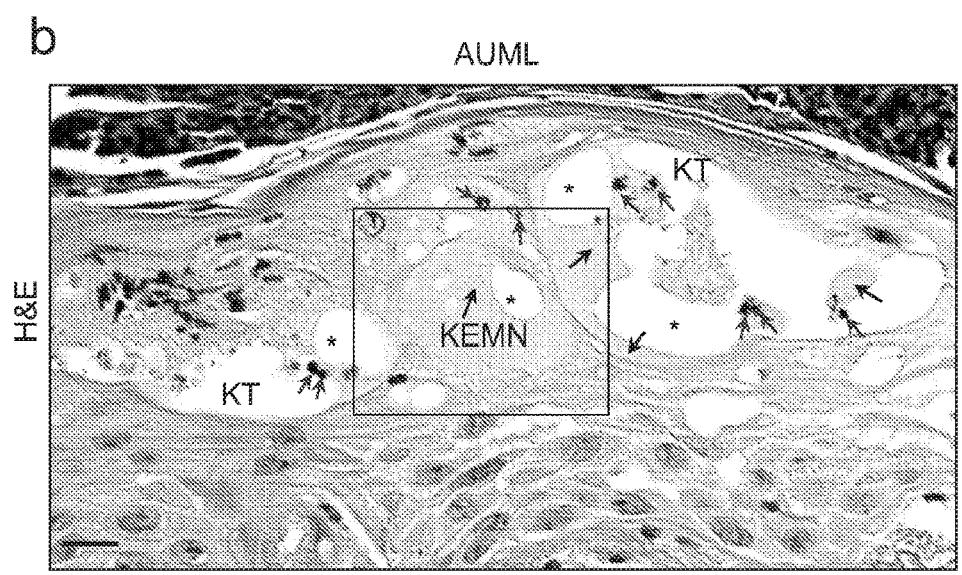
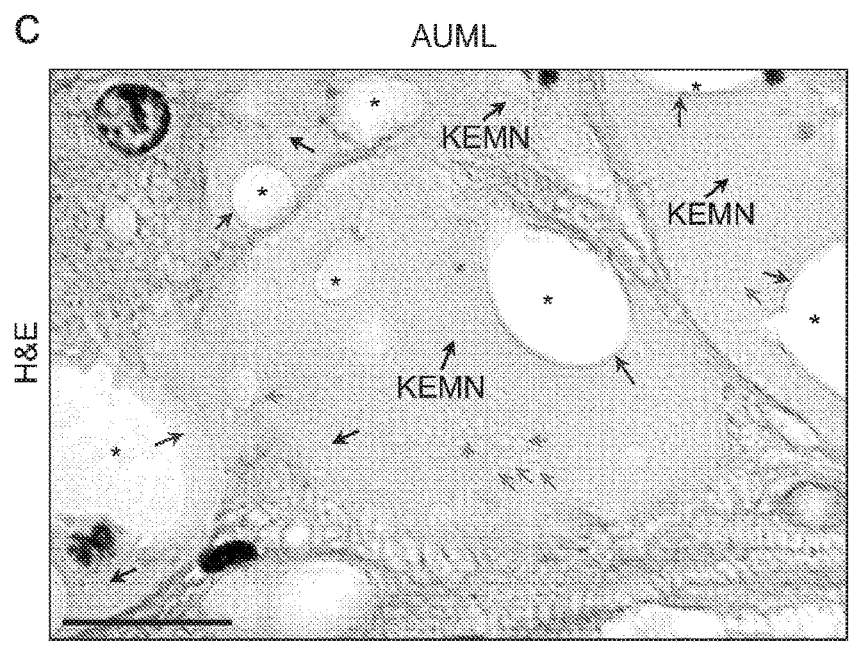

FIG. 14A-C
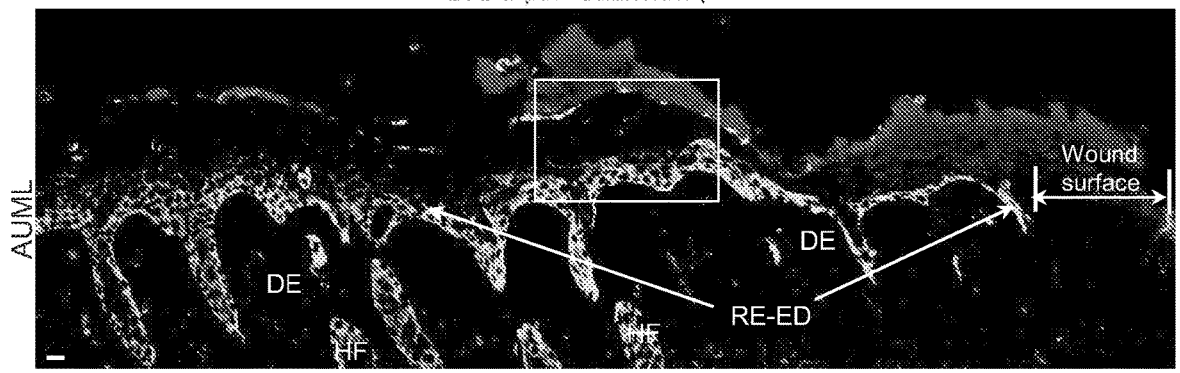
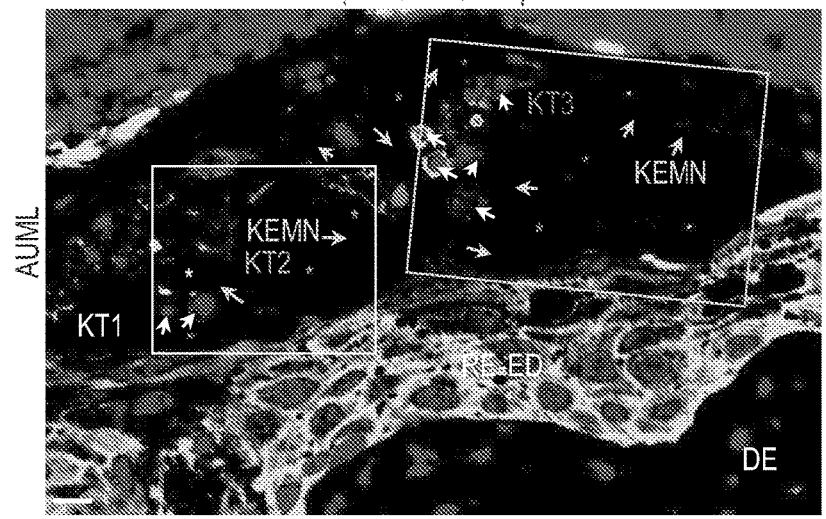
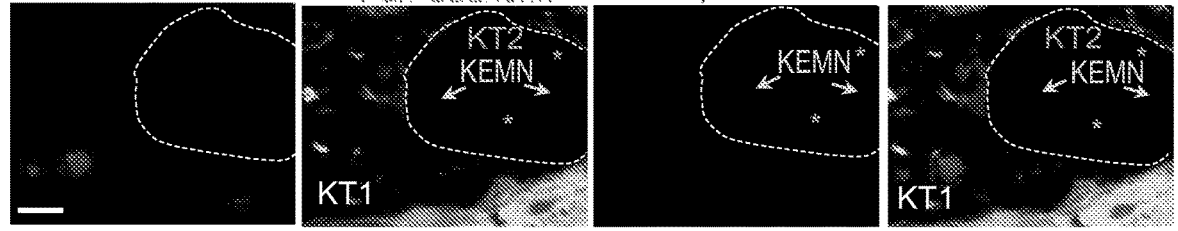

FIG. 15A-B
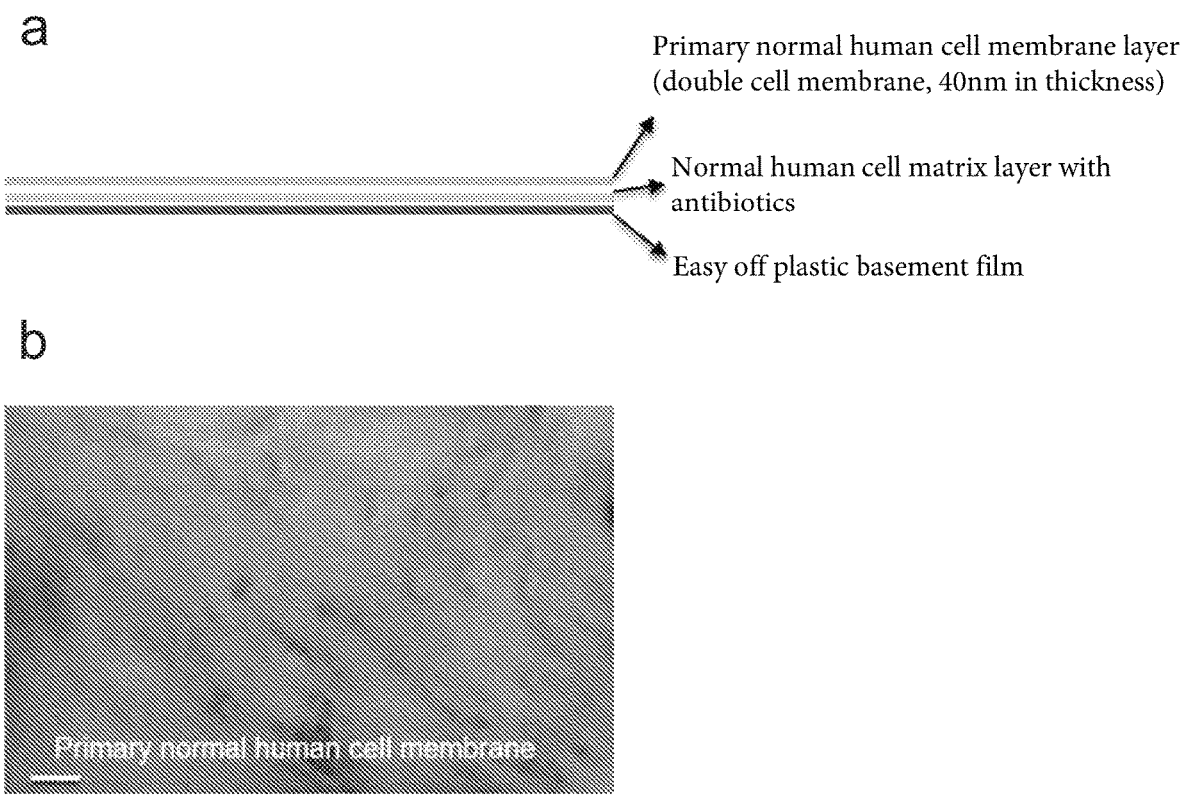

METHODS FOR GENERATION OF CELL-DERIVED MICROFILAMENT NETWORK

RELATED APPLICATION DATA

This application claims priority to U.S. Provisional Application No. 62/485,422 filed on Apr. 14, 2017, which is hereby incorporated herein by reference in its entirety for all purposes.

STATEMENT OF GOVERNMENT INTERESTS

This invention was made with government support under CA068262 awarded by the National Institutes of Health. The government has certain rights in the invention.

FIELD

The invention is directed to methods and compositions useful for wound healing and tissue regeneration.

BACKGROUND

Wound repair involves complex biological processes, and managing wounds with a large surface area is a great challenge (Singer, A. J. & Clark, R. A. Cutaneous wound healing. The New England journal of medicine 341, 738-746 (1999), Passier, R., van Laake, L. W. & Mummery, C. L. Stem-cell-based therapy and lessons from the heart. Nature 453, 322-329 (2008)). Over 100 million patients in the industrialized world suffer from wounds every year (Takeo, M., Lee, W. & Ito, M. Wound healing and skin regeneration. Cold Spring Harbor perspectives in medicine 5, a023267 (2015)). In mammalian organs, immediately after an injury occurs the broken and/or affected cells release various molecules that induce diverse intracellular and intercellular pathways within the immune system, the blood coagulation cascade, the inflammatory pathways, and any neighboring uninjured cells (Gurtner, G. C., Werner, S., Barrandon, Y. & Longaker, M. T. Wound repair and regeneration. Nature 453, 314-321 (2008)). During normal responses to injury, many types of cells, including neutrophils, monocytes, lymphocytes, endothelial cells, keratinocytes, fibroblast, and stem cells and their derivatives, undergo remarkable changes in signal transduction, gene expression, and phenotype, leading to cell migration, proliferation, and differentiation (Lane, S. W., Williams, D. A. & Watt, F. M. Modulating the stem cell niche for tissue regeneration. Nature biotechnology 32, 795-803 (2014)). Dynamic and reciprocal cell-extracellular matrix (ECM) and cell-cell interactions precisely orchestrate the activation and shutdown of various pathways during the complex processes of inflammation, new tissue formation, and remodeling. Some eukaryotic organisms retain the ability to completely replicate original tissue structures and functions throughout their adult lives via regeneration, a process that is still poorly understood. For unknown reasons, humans exhibit this ability only during prenatal development (Zielins, E. R. et al. Wound healing: an update. Regenerative medicine 9, 817-830 (2014)). Pathophysiology can lead to impaired healing, as seen in non-healing ulcers, or to "overhealing" as found in hypertrophic scars and keloids. Furthermore, inappropriate interventions can trigger malignant transformation (Chidgey, A. P., Layton, D., Trounson, A. & Boyd, R. L. Tolerance strategies for stem-cell-based therapies. Nature 453, 330-337(2008)). Despite the promise of stem cells in the translational studies, the use of allogeneic and autogeneic stem cell therapies in clinical wound healing modalities still faces a number of regulatory hurdles (Rose, L. F. & Chan, R. K. The Burn Wound Microenvironment. Advances in wound care 5, 106-118 (2016)). The management of complex, chronic, and large-area wounds in humans remains a challenge.

To be considered appropriate for use in wound treatment, materials/agents should promote reepithelialization and wound healing without inducing neoplasm development, minimize pain, decrease the risk of infection, and reduce cosmetic deformity; the selection of such materials is a major component of modern wound management and regenerative medicine (Lutolf, M. P. & Hubbell, J. A. Synthetic biomaterials as instructive extracellular microenvironments for morphogenesis in tissue engineering. Nature biotechnology 23, 47-55 (2005)). Currently available man-made wound-healing matrices are synthetic and/or contain natural biomimetic materials fabricated using various techniques; such materials include silicone, biobrane, nanofibrillar, supramolecular materials, and scaffolds presenting individual or multiple biochemical ECM-derived signals (Warner, P. M., Coffee, T. L. & Yowler, C. J. Outpatient burn management. The Surgical clinics of North America 94, 879-892 (2014); Hubbell, J. A. Biomaterials in tissue engineering. Bio/technology 13, 565-576 (1995)). The ECM is composed of an interlocking mesh of cell-secreted proteins and glycosaminoglycans. The native ECM possesses biophysical properties of surface topology, bulk stiffness, elasticity, shear force, and pore size that are important for cue-guided cell migration and stem cell differentiation. In addition, the ECM also anchors diverse soluble growth factors, signal receptors and adhesion molecules, which influence cell fates. Reconstituted ECM and ECM-derived materials may lack the native topology information, soluble growth factors and anchored factor concentrations. Despite the sustainable advance of the present technologies, large-area ($ft^2$-scale) native biomaterials containing the complete and native ECM biophysical, biochemical, and biomechanical properties that make them ideal materials for use in wound repair are currently not available (Chien, K. R. Regenerative medicine and human models of human disease. Nature 453, 302-305 (2008)).

Wound infection continues to be a challenging problem and represents a considerable healthcare burden. The physical barrier at wounds to prevent micro-organism contamination and colonization is essential for wound infection prevention. Wounds (acute or chronic) usually contain micro-organisms, including bacteria, fungus and virus (Sood, A., Granick, M. S., and Tomaselli, N. L. (2014) Wound Dressings and Comparative Effectiveness Data. Advances in wound care 3, 511-529, Lall, R. R., Wong, A. P., Lall, R. R., Lawton, C. D., Smith, Z. A., and Dandaleh, N. S. (2014) Evidence-based management of deep wound infection after spinal instrumentation. Journal of clinical neuroscience: official journal of the Neurosurgical Society of Australasia, Misic, A. M., Gardner, S. E., and Grice, E. A. (2014) The Wound Microbiome: Modern Approaches to Examining the Role of Microorganisms in Impaired Chronic Wound Healing. Advances in wound care 3, 502-510). The presence of bacteria in a wound may lead to wound contamination, colonization and infection (Adam, E. N., and Southwood, L. L. (2006) Surgical and traumatic wound infections, cellulitis, and myositis in horses. The Veterinary clinics of North America. Equine practice 22, 335-361, viii). During wound infection, bacteria multiply, healing is disrupted and wound tissues are damaged (local infection) (Gomathysankar, S., Halim, A. S., and Yaacob, N. S. (2014)

Proliferation of keratinocytes induced by adipose-derived stem cells on a chitosan scaffold and its role in wound healing, a review. *Archives of plastic surgery* 41, 452-457, Grazul-Bilska, A. T., Johnson, M. L., Bilski, J. J., Redmer, D. A., Reynolds, L. P., Abdullah, A., and Abdullah, K. M. (2003) Wound healing: the role of growth factors. *Drugs of today* 39, 787-800). Bacteria may result in spreading infection in nearby tissues or systemic infection which presents systemic illness. Acute wounds include surgical and traumatic wounds, and burns (Palmieri, T. L., Przkora, R., Meyer, W. J., 3rd, and Carrougher, G. J. (2014) Measuring burn injury outcomes. *The Surgical clinics of North America* 94, 909-916, Jeng, J., Gibran, N., and Peck, M. (2014) Burn care in disaster and other austere settings. *The Surgical clinics of North America* 94, 893-907). For instance, approximately 500,000 persons seek medical treatment for burns every year in the United States alone (Heard, J. P., McDonald, K. M., Xing, Y., Kluesner, K. M., Liao, J., and Wibbenmeyer, L. A. (2014) Regional and National Review of Factors Associated With Burn Wound Cellulitis. *Journal of burn care & research: official publication of the American Burn Association*). Chronic wounds include diabetic foot ulcers, venous leg ulcers, arterial leg/foot ulcers and pressure ulcers (Moran, M. E. (2014) Scleroderma and evidence based non-pharmaceutical treatment modalities for digital ulcers: a systematic review. *Journal of wound care* 23, 510-516, Baltzis, D., Eleftheriadou, I., and Veves, A. (2014) Pathogenesis and treatment of impaired wound healing in diabetes mellitus: new insights. *Advances in therapy* 31, 817-836). Although effective management of wound infection requires a multidisciplinary approach, physical barriers to protect the injured tissues from micro-organisms is an optimal infection control procedure (Cheadle, W. G. (2006) Risk factors for surgical site infection. *Surgical infections* 7 Suppl 1, S7-11).

Native cell cytoplasm membrane is a bi-lipid membrane harboring thousands of membrane proteins modified by phosphor, sugar chains, and so on. Cell cytoplasm membrane can effectively form physical barriers for micro-organism infection (Hahler, B. (2006) Surgical wound dehiscence. *Medsurg nursing: official journal of the Academy of Medical-Surgical Nurses* 15, 296-300; quiz 301). However, the area of cytoplasm membrane of a single cell is too small ($\mu m^2$ level) to be applied for clinical usage. The fragility and tiny thickness (5~10 nm) of cell membrane make it difficult to collect cytoplasm membranes of multiple cells and reorganize them into a useful membrane for wound care. There remains a need for large-area membranes useful for wound repair and effective prevention and management of wound infection.

SUMMARY

The present disclosure addresses this need and is based on the discovery that native primary human epithelial cells grown in matrix support produce large-area microfilament network. According to one aspect, the microfilament network functions as physical barrier for prevention and management of wound infection, including chronic and acute wounds, burn care, acute and surgical wound care. As presented herein, normal primary human epithelial cells cultured on cell matrix generate a large-area of microfilament network. According to another aspect, the microfilament network is processed to remove the cells or nuclei. According to one aspect, the microfilament network can be applied to wounds and acts as physical barrier to prevent micro-organism induced wound infection. The engineered large area microfilament network-matrix complex layer can effectively prevent infection by micro-organisms, including bacteria, fungi and viruses.

Microfilaments, the main cytoskeletal polymers in eukaryotic cells, are polymerized by actin subunits and actin-binding proteins. Microfilaments are essential for cell division and cytokinesis, cell shape maintenance, vesicle transportation, signal transduction and cell motility. Most animal cells maintain a micrometer ($\mu m$)-scale cell size, which restricts the area of the cytoskeletal microfilament networks to the same scale. According to certain aspects, human epithelial cell masses cultured in vitro on matrigel generate super large extracellular microfilament networks (EMNs). Such EMNs facilitate cell migration. According to one aspect, these EMNs can grow to square foot ($ft^2$) size. According to another aspect, these microfilament networks have utility in a general wound healing therapy. According to certain aspects, the EMNs generated by human epithelial cell masses contain extensive membrane-enclosed microfilaments. According to one aspect, the microfilament network is treated to remove cell masses to produce artificial, cell-less, and $ft^2$-scale, ultra-large multi-layered lattices (UMLs). According to another aspect, these UMLs can be used to facilitate the reepithelialzation. According to yet another aspect, these UMLs have utility for healing of second degree thermal burn wounds in mice. According to certain aspects, the EMNs produced by human epithelial cells promote/facilitate cell migration. According to one aspect, the UMLs obtained after cell removal can be used to facilitate wound healing and tissue regeneration.

In one aspect, embodiments of the present disclosure are directed to networks including cell-derived microfilaments interconnected in a continuous lattice or mesh structure between a plurality of microfilament source regions.

In another aspect, embodiments of the present disclosure are directed to methods of producing a network of microfilaments including the steps of: culturing cells in a matrix support and cell culture medium wherein the cells proliferate and form aggregated cell masses, and wherein the cell masses produce microfilaments external to and surrounding the cell masses, and wherein the extracellular microfilaments connect and form a continuous extracellular microfilament network. In certain embodiments, the network of microfilaments is treated to remove nuclei of the cells and/or the cells from the network. In one embodiment, the cell masses form on top of the matrix support.

In one embodiment, the microfilaments of the network are extracellular microfilaments. In another embodiment, the microfilaments are membrane-enclosed. In one embodiment, the microfilaments include actin. In another embodiment, the actin includes β-actin. In one embodiment, the microfilaments are about 1-1000 µm in length. In another embodiment, the microfilaments are branched. In yet another embodiment, the microfilaments have about 2-10 branches. In one embodiment, multiple microfilaments align together and form bundles of diverse architectural structures. In another embodiment, the microfilament source regions form connection nodes for the continuous lattice or mesh structure. In one embodiment, the network further includes adhesive materials. In one embodiment, the adhesive materials associate with the microfilaments and enlarge the diameter of the microfilaments. In one embodiment, the network has an area in the range of about 1 $\mu m^2$ to about 500 $cm^2$ and a thickness in the range of about 1 nm to about 0.5 cm. In another embodiment, the network is single or multiple layered. In yet another embodiment, the surface area of the microfilaments is greater than an equivalent unit of an intra-cellular cytoskeletal microfilament network surface area.

In one embodiment, the network is porous. In one embodiment, the pore size ranges from about 0.1-5 μm in diameter. In one embodiment, the network further includes bioactive and/or bioinactive agents. In another embodiment, the bioactive agents are therapeutic drugs. In one embodiment, the microfilament source regions include cells. In another embodiment, the network is present on a matrix support. In yet another embodiment, the matrix support is biodegradable. In one embodiment, the network is present on a Matrigel matrix support. In one embodiment, the network lacks nuclei from cells. In another embodiment, the network lacks cells. In one embodiment, the microfilament source regions include eukaryotic cells with or without genetic modification. In one embodiment, the eukaryotic cells are mammalian cells. In another embodiment, the mammalians cells are human cells. In yet another embodiment, the human cells are human mammary epithelial cells. In one embodiment, the microfilaments are embedded within the top surface of the matrix support. In one embodiment, the matrix is a Matrigel. In one embodiment, the matrix support inhibits cell attachment and migration.

In still another aspect, the present disclosure provides a method for treating a medical condition via applying the microfilament network of to an area in need of treatment. In one embodiment, the microfilament network is applied with the matrix. In another embodiment, the microfilament network is applied without the matrix. In one embodiment, the medical condition is a wound or an injured tissue. In another embodiment, the microfilament network facilitates healing and/or prevents infection of the wound or the injured tissue. In one embodiment, the medical condition is a burn. In one embodiment, the method includes enhancing or promoting re-epithelialization of damaged skin. In another embodiment, the method further includes administering therapeutic drugs prior to, concurrent with or after applying the microfilament network to the area in need of treatment.

In a related aspect, the present disclosure contemplates a method of producing a continuous network of cell-derived microfilaments in vitro including: culturing a plurality of cell clusters on a surface of a matrix substrate under conditions such that the cell clusters produce microfilaments external to and surrounding the cell clusters, and where the extracellular microfilaments connect and form a continuous extracellular network of microfilaments between the cell clusters on the surface of the matrix substrate. In one embodiment, the cell clusters are spaced apart by an average distance of between about 1 microns and about 1000 microns. In another embodiment, the microfilaments connecting the cell clusters have an average length of between about 1 microns and about 1000 microns. In one embodiment, the continuous extracellular microfilament network is a multilayered lattice. In another embodiment, the microfilaments are branched. In one embodiment, the continuous extracellular microfilament network is a multilayered lattice including long microfilaments having a length of between about 10 microns and about 1000 microns and short microfilaments having a length of between about 1 microns and about 10 microns. In another embodiment, the continuous extracellular network of microfilaments has a surface area of between about 0.01 cm$^2$ and 500 cm$^2$. In one embodiment, the continuous extracellular microfilament network is a mesh. In another embodiment, the continuous extracellular microfilament network is porous. In one embodiment, cells are implanted on the surface of the matrix substrate and where the cells migrate and aggregate into preclusters and proliferate to form the cell clusters. In another embodiment, the method further includes removing cell nuclei or the cell clusters from the continuous extracellular microfilament network. In one embodiment, the matrix substrate inhibits attachment and/or migration of the cells. In another embodiment, the method further includes separating the matrix substrate from the continuous extracellular microfilament network.

According to another aspect, a method is provided for facilitating wound repair and/or tissue regeneration comprising applying the microfilament network to a site in need thereof. In certain embodiments, the microfilament network is applied with or without the matrix. In one embodiment, the microfilament network forms square foot (ft$^2$)-scale ultra-large microfilament lattices (UMLs). In another embodiment, the UMLs construct an environment for cell migration. In one embodiment, the microfilament networks are multilayered and three dimensional (3D). In another embodiment, the method includes removing cell masses and producing acellular UMLs (AUMLs). In one embodiment, the AUMLs facilitate wound repair. In another embodiment, the method includes applying the AUMLs to a wounded site. In one embodiment, applying the AUMLs allows keratinocytes to engender large tunnels in the reepithelialized epidermis. In another embodiment, the large tunnels provide pathways for cells and nutrients to the site of wound repair. In certain embodiment, the microfilament network prevents infection of the wounded site. In one embodiment, method includes enhancing or promoting re-epithelialization of wounded skin. In another embodiment, the wound is second degree thermal burn wounds. In yet another embodiment, method further includes administering therapeutic drugs prior to, concurrent with or after applying the microfilament network to the area in need of treatment.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIGS. 1A-F show images of human mammary epithelial cells (HMECs) forming masses on the Matrigel matrix. FIG. 1A depicts that the individual human mammary epithelial cells (HMECs) in the 2D environment present as irregular shapes shapes (left) while consistently display a spherical morphology in the 3D (three-dimensional) Matrigel culture on the (right). HMECs were implanted on the thick Matrigel matrix (20~30 µm in depth) at a low cell density (1×10³ cells per well in 6-well-plates). The inverted phase contrast images were taken at 5 hours (h) after cell implantation. FIG. 1B is a representative toluidine blue image showing a cross section of a spherical HMEC with a minimal surface area exposed to the Matrigel matrix (MM). FIG. 1C is a representative toluidine blue image of a cross section of a cell group showing that two spherical stacked HMECs (white asterisks) have no surface contact with the Matrigel matrix (MM). FIG. 1D is a representative toluidine blue image of a cross section of a mounded cell mass showing that multiple stacked HMECs (white asterisks) are not in contact with the Matrigel matrix (MM). FIG. 1E is a representative inverted phase contrast image showing that the HMECs form many cell masses after cell migration, aggregation, proliferation and stacking. FIG. 1F is a representative hematoxylin and eosin (H&E) staining image showing that the cell masses generate a superlarge mesh (red arrows) exterior to the cell masses, surrounding the cell masses and covering the entire Matrigel surface in wells (6-well-plate) or 10 cm dishes. There are many large (>40 µm in diameter) and round holes (blue arrows) in the superlarge mesh. The edges (green arrows) of the holes are shown. Scale bar=10 µm.

FIGS. 2A-B show fluorescent images that human cell masses generate superlarge and continuous extracellular microfilament networks. FIG. 2A shows fluorescence microscopy examination of the composition and architecture of the extracellular microfilament networks. Plasmids encoding enhanced green fluorescence protein (EGFP) tagged-plasma membrane Ca²⁺-ATPase2 (EGFP-PMCA2) were transiently transfected into primary normal human mammary epithelial cells (HMECs). HMECs with EGFP-PMCA2 overexpression were transplanted onto the Matrigel matrix surface and cultivated for 64 hours (h). HMECs migrated, aggregated, proliferated, and formed cell masses (CMs) on the Matrigel layers. Left panel: DAPI (4',6-diamidino-2-phenylindole) staining image shows that there are no cell nuclear materials between and around the cell masses. Middle panel: the cell masses generate a large quantity of membrane-enclosed, long, branched extracellular microfibers (ECMFs, white arrows) exterior to the cell masses. The nested microfibers form large networks surrounding the cell masses. The long extracellular microfibers (bold white arrows) connect the two cell masses (CM1 and CM2). Right panel: the merged image shows that the nested extracellular microfiber networks are located exterior to the cell masses that generate them. FIG. 2B shows fluorescent images of actin-composed microfilaments. The plasmids encoding EGFP-PMCA2 and mCherry tagged-β-actin (mCherry-β-actin) were transiently co-transfected into HMECs. The cell masses (CM)-produced microfibers are actin-based and membrane-enclosed extracellular microfilaments (ECMFs, white arrows). The extracellular microfilaments form networks and bundles (yellow arrows). An extracellular microfilament connection node (EMCN, purple arrows), an extracellular microfilament assembled network space (EMNS, white asterisks), and microfilament adhesive materials (AMs) are shown. Scale bar=20 µm.

FIGS. 4A-D are images showing that the number of extracellular microfilaments and microfilament connection nodes increase rapidly, quickly forming multi-layered 3D extracellular microfilament networks. Scale bar=20 µm. FIG. 4E shows the quantitative analyses of increases in extracellular microfilament during development (mean±s.d., n=5 areas at each time point, each area is located directly between two HMEC masses).

FIG. 5A shows a merged fluorescence image that extracellular microfilaments (ECMF, red arrows) connect via extracellular microfilament connection nodes (EMCN, purple arrows) with regularly and irregularly-shaped spaces (asterisks). Triangular (white asterisk), quadrilateral (purple asterisks) and pentagonal (yellow asterisk) spaces in an extracellular microfilament network are shown. A large bundle (cyan arrow) is formed by several long, parallel, and twisted extracellular microfilaments. The area framed with white dashes is enlarged and shown in (b). FIG. 5B shows two extracellular microfilaments twist and form a twisted bundle with two rings (blue arrows). FIG. 5C is a cartoon showing the twisted bundle with rings in (b). Scale bar=10 µm.

FIG. 6A shows fluorescence images of a part of a superlarge, continuous, extracellular microfilament network made up of multiple networks in a 10 cm dish. HMECs with EGFP-PMCA2 overexpression were transplanted onto the Matrigel matrix surface and cultivated for 80 h. Two cell masses and the extracellular microfilament network surrounding them are shown. There are several unknown membrane enclosed round bodies without nuclear materials (white arrows) scattered in the superlarge network. The white-framed area in the merged image is enlarged and shown in (b). FIG. 6B shows the enlarged image of the white-framed area in (FIG. 6A). The extracellular microfilament networks of the two cell masses widely connect and form a continuous superlarge network complex with no interruption. The focused top layer and the unfocused lower layer in the same superlarge network are shown. There are large quantities of small pores (white asterisks, pore size range: 0.1~5 µm) throughout the multi-layered extracellular microfilament network. Scale bar=20 µm.

FIGS. 8A-C show a schematic diagram and images of generation of 500 cm², ultra-large scale and cell-less extracellular microfilament assembled network complexes. FIG. 8A shows a schematic diagram of generation of artificial, 500 cm² superlarge and HMEC mass-engendered microfilament network complex. HMECs are implanted on Matrigel matrix layers in the cell culture media. HMECs migrate, aggregate, proliferate, and form cell masses. Subsequently, the cell masses generate long, branched, and membrane-enclosed extracellular microfilaments. Nested extracellular microfilaments form networks exterior to and surrounding the cell masses. The extracellular microfilament networks connect and form a 500 cm$^2$ continuous, ultra-large lattice covering the entire Matrigel surface. After artificial decellularization, a 500 cm$^2$ ultra-large-scale, cell-less, extracellular microfilament network (EMN, red arrow) is produced. FIG. 8B shows a hematoxylin and eosin (H&E) staining image of part of a superlarge continuous HMEC extracellular microfilament network (EMN, red arrows) with cell masses (CMs, blue arrows) on the Matrigel matrix surface of a 500 cm$^2$ plate. There is no large (diameter ≥20 μm) round hole caused by the disassembly of extracellular microfilament network at this stage. Scale bar=10 μm. FIG. 8C shows a H&E staining image showing part of a cell-less, 500 cm$^2$ ultra-large scale extracellular microfilament EMN (red arrows) after artificial decellularization. Scale bar=10 μm.

FIGS. 9A-C show that acellular ultra-large microfilament lattices (AUMLs) promote the reepithelialization and healing of deep second degree thermal burn wounds and the generation of keratinocyte tunnels and EMNs in the reepithelialized epidermis. (FIG. 9A) shows statistical analyses of the effects of AUMLs on the deep second degree thermal burn wound healing at 14 day post-burn (dpb). Student t-test; 2-tailed; n=5 mice in each group. (FIG. 9B) shows keratinocytes forming large tunnels in the reepithelialized epidermis (RE-ED). A representative immunofluorescence image shows that there are multiple keratinocyte tunnels (KTs) in the RE-ED in the AUML treated wounds. The large KT1 lumen contains many cells of different types. The KT2 lumen harbors keratinocyte EMNs. The framed KT1 and KT2 areas are enlarged in FIGS. 11B-C, respectively. Dermis (DM) and hair follicles (HF) are shown. Scale bar=10 μm. (FIG. 9C) is a scatterplot of the total occurrence of keratinocyte tunnels in 5 wound sectioned specimens (each specimen is randomly selected from the wound specimens of a mouse, n=5 mice of each group, Wilcoxon rank-sum test after Bonferroni correction, P<10$^{-15}$). Each black dot represents a keratinocyte tunnel. (FIG. 9D) The enlarged area in FIG. 14B. A representative immunofluorescence image shows that a large keratinocyte tunnel (KT, labeled with purple dashed lines) lumen contains large keratinocyte EMNs (KEMNs), which supply scaffolds and environments for cell migration and behavior (white arrows). The keratinocyte EMNs (orange arrows) and irregular holes (purple asterisks) caused by the keratinocyte EMN decomposition are shown.

FIGS. 10A-B show AUMLs facilitate the re-epithelization and healing of second degree thermal burn wounds and allow the generation of keratinocyte tunnels. (FIG. 10A) shows representative images of second degree thermal cutaneous burn wounds with/without treatment of Mepiform or AUMLs in mice at different day post-burn (dpb). (FIG. 10B) shows representative H&E images of sectioned specimens of the burn wounds from each mouse group at 14 dpb. There are two large keratinocyte tunnels (KTs) with multiple cells in the reepithelialized epidermis (RE-ED) in the wounds with AUML treatment, but not in the wounds from the group without treatment or treated with Mepiform. The blue-framed area is shown in FIG. 11A. Reepithelialized epidermis (RE-ED) and dermis (DE) are shown.

FIGS. 11A-C show keratinocyte tunnels and EMNs provide avenues for cell transport in the reepithelialized epidermis in the AUML treated wounds. (FIG. 11A) shows enlarged area in the framed area in FIG. 10B. There are two large keratinocyte tunnels in the reepithelialized epidermis of the wounds treated with AUML. In the keratinocyte tunnel-1 (KT1) lumen, there are multiple red blood cells (RBC, black arrows) and keratinocyte EMN (KEMN) fragment (blue arrow). In the KT2 lumen, there is a keratinocyte EMN (KEMN, blue arrow) with diverse types of cells migrating in/on it, including red blood cells and nucleated cells (cyan arrows). (FIG. 11B) shows enlarged area in the framed area (in white) in FIG. 9B. There are multiple different types of cells migrate in the lumen of keratinocyte tunnel-1 (KT1), including red blood cells (purple arrows), and an orthochromative normoblast (ON) with fully matured cytoplasm and a small, compact, and pycnotic nucleus (white arrow). (FIG. 11C) shows enlarged area in the framed area (in orange) in FIG. 9B. There is a keratinocyte EMN (KEMN) in the lumen of keratinocyte tunnel-2 (KT2). The membrane-enclosed and extracellular microfilament composed keratinocyte EMN (KEMN, orange arrows) is shown. A nucleated cell (white arrow) migrates in the keratinocyte EMN. Scale bar is 20 μm in (a) and 10 μm in (B-C).

FIGS. 12A-C show keratinocyte tunnels and EMNs provide pathways for cell transport and migration in the reepithelialized epidermis in the AUML treated wounds. (FIG. 12A) is a representative H&E staining image shows that there are two keratinocyte tunnels (KT1 and KT2) in the reepithelialized epidermis in the wounds with AUML treatment. The framed areas (KT1 and KT2) are enlarged and shown in (b) and (c) respectively. Reepithelialized epidermis (RE-ED) and dermis (DE) are shown. (FIG. 12B) shows many mature enucleated red blood cells (RBCs, black arrows) migrate in the large keratinocyte EMN (KEMN) in the KT1 lumen. (FIG. 12C) shows two nucleated cells migrate in the large keratinocyte tunnel-2 (KT2).

FIGS. 13A-C show keratinocyte EMNs supply scaffolds for cell migration and behavior in the keratinocyte tunnel lumen and keratinocyte EMNs disassemble. (FIG. 13A) is a representative H&E staining image shows that keratinocyte EMN complexes are formed in the large keratinocyte tunnel lumens in the reepithelialized epidermis in the AUML treated wounds. Reepithelialized epidermis (RE-ED) and dermis (DE) are shown. The framed area is enlarged and shown in (B). (FIG. 13B) shows the enlarged area in (A). Many cells (blue arrows) locate in the keratinocyte EMN (KEMN) complexes in disassembling in the lumen of a large keratinocyte tunnel (KT). The black arrows show the keratinocyte EMN fragments and the black asterisks show the big holes (or cross sections of big channels) caused by the disassembly of keratinocyte EMN complex. The farmed area is enlarged and shown in (C). (FIG. 13C) shows the archeology of keratinocyte EMNs. The keratinocyte extracellular microfilament composed EMNs (KEMN, black arrows) contains large quantities of irregular-shaped pores (green arrows) in various sizes. The disassembly of keratinocyte EMNs leads to many channels (black asterisks) in the keratinocyte EMNs. The edges (blue arrows) of the channels in the keratinocyte EMNs are shown.

FIGS. 14A-C show keratinocyte EMN complexes build environments for cells, and keratinocyte ECMFs disassembly leads to keratinocyte EMN decomposition. (FIG. 14A) is a representative immunofluorescence image shows that AUMLs allow reepithelialized epidermis to form keratinocyte tunnel complexes harboring keratinocyte EMNs in different stages. Reepithelialized epidermis (RE-ED), dermis (DE) and hair follicles (HF) are shown. The framed area is shown in (b). (FIG. 14B) shows there is a keratinocyte tunnel complex containing three neighboring keratinocyte tunnels (KT1, KT2 and KT3). The keratinocyte EMN (KEMN) in KT1 lumen is largely decomposed with a small channel (white asterisk) in the remained keratinocyte EMN. The majority of keratinocyte EMN in KT2 lumen is integrity while two channels (cyan asterisks) present in this EMN. The large keratinocyte EMN in KT3 lumen is decomposed and divided into several big or small EMN fragments. Multiple cells (white arrows) locate in the keratinocyte EMNs in the KT3 lumen. The framed areas in white and orange are show in Supplementary FIG. 12c and FIG. 3, respectively. (FIG. 14C) is a representative fluorescence image shows that the disassembly of keratinocyte membrane-enclosed microfilaments leads to decomposition of keratinocyte EMNs (KEMN, orange arrows) forming channels in the EMNs (cyan arrows).

FIGS. 15A-B show the generation of large area primary normal human cell membranes. FIG. 14A is a schematic diagram of large area primary normal human cell membrane generation. Cell membrane layer is about 40 nm in depth. FIG. 14B is a representative image of a part of native primary normal human cell membrane (eosin stained) on Matrigel matrix in a 10 cm (diameter) dish. Scale bar=100 μm.

DETAILED DESCRIPTION

Figure 3:
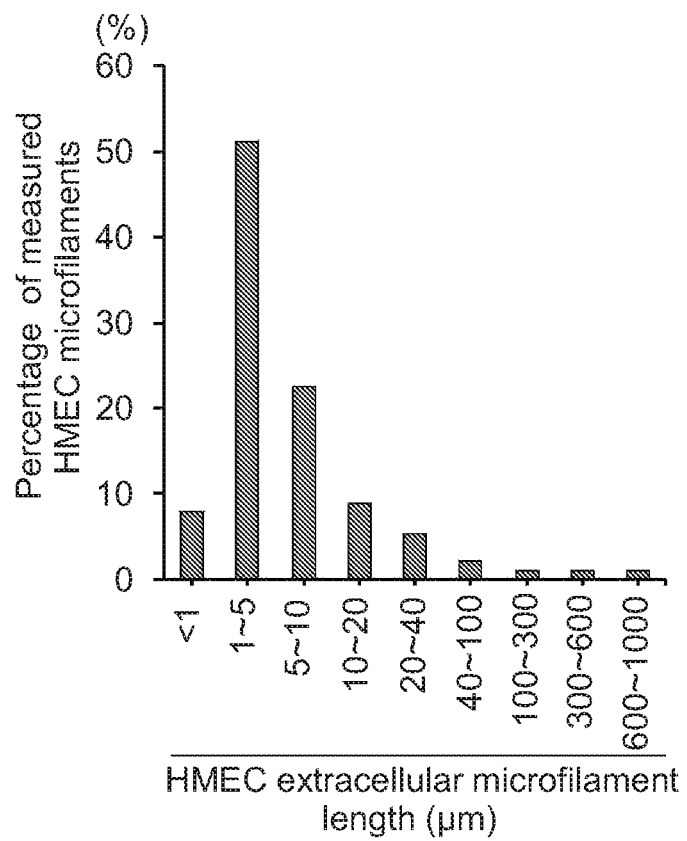
FIG. 3 shows the distribution of the length of extracellular microfilaments. Distribution of the lengths of a total of 385 randomly chosen HMEC extracellular microfilaments: approximately 51% are in the range of 1~5 µm, 22.6% in the range of 5~10 µm, 8.9% in the range of 10~20 µm, 5.2% in the range of 20~40 µm, 2% in the range of 40~100 µm, 1% in the range of 100~300 µm, and 2% reach up to 1000 µm.
Figure 4:
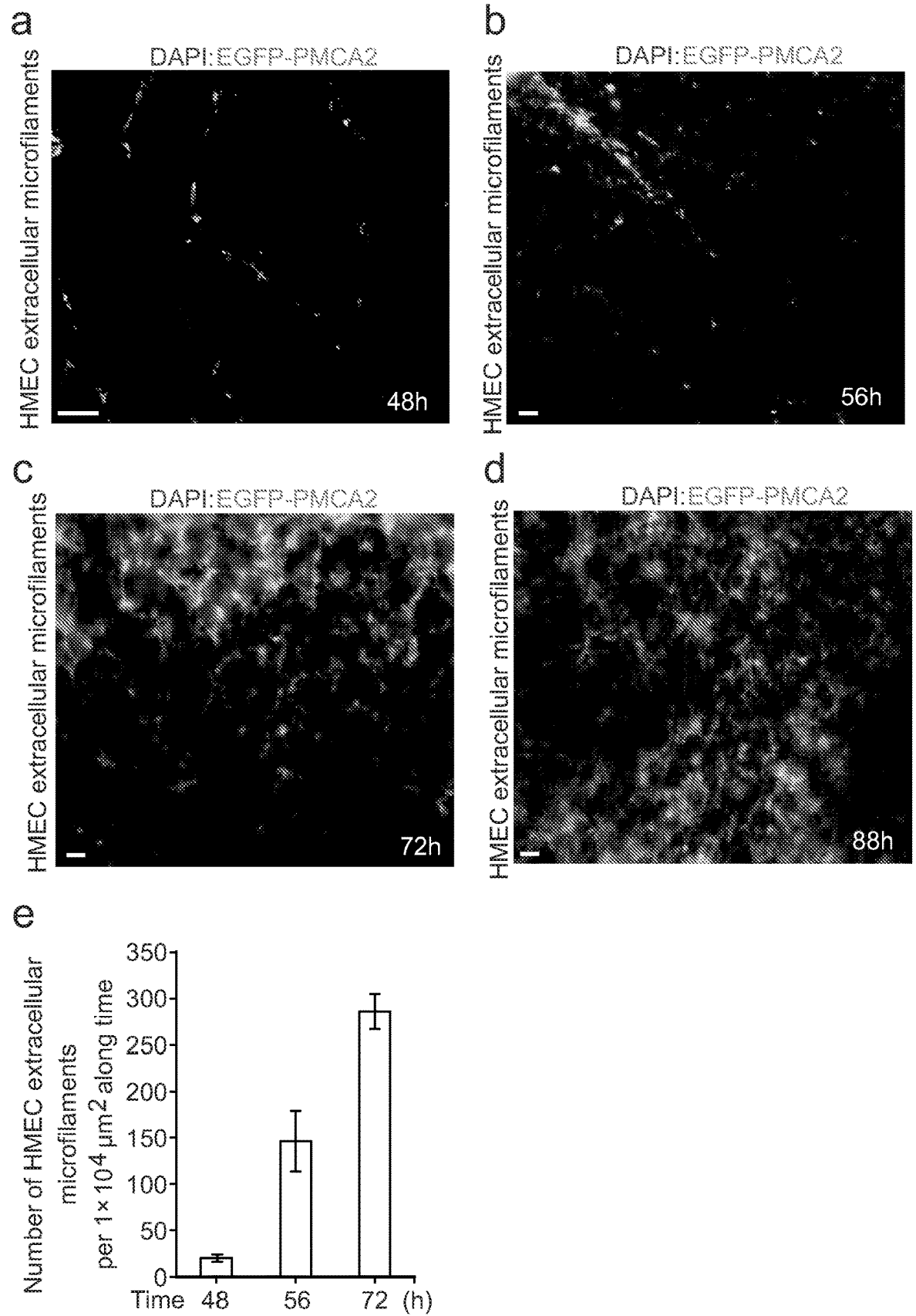
FIGS. 4A-E show fluorescent images and bar graphs of development of the extracellular microfilament networks. Representative fluorescence images of the HMEC extracellular microfilament network development along time. HMECs with EGFP-PMCA2 overexpression were transplanted onto the Matrigel matrix surface and cultivated for a period of time.
Figure 5:
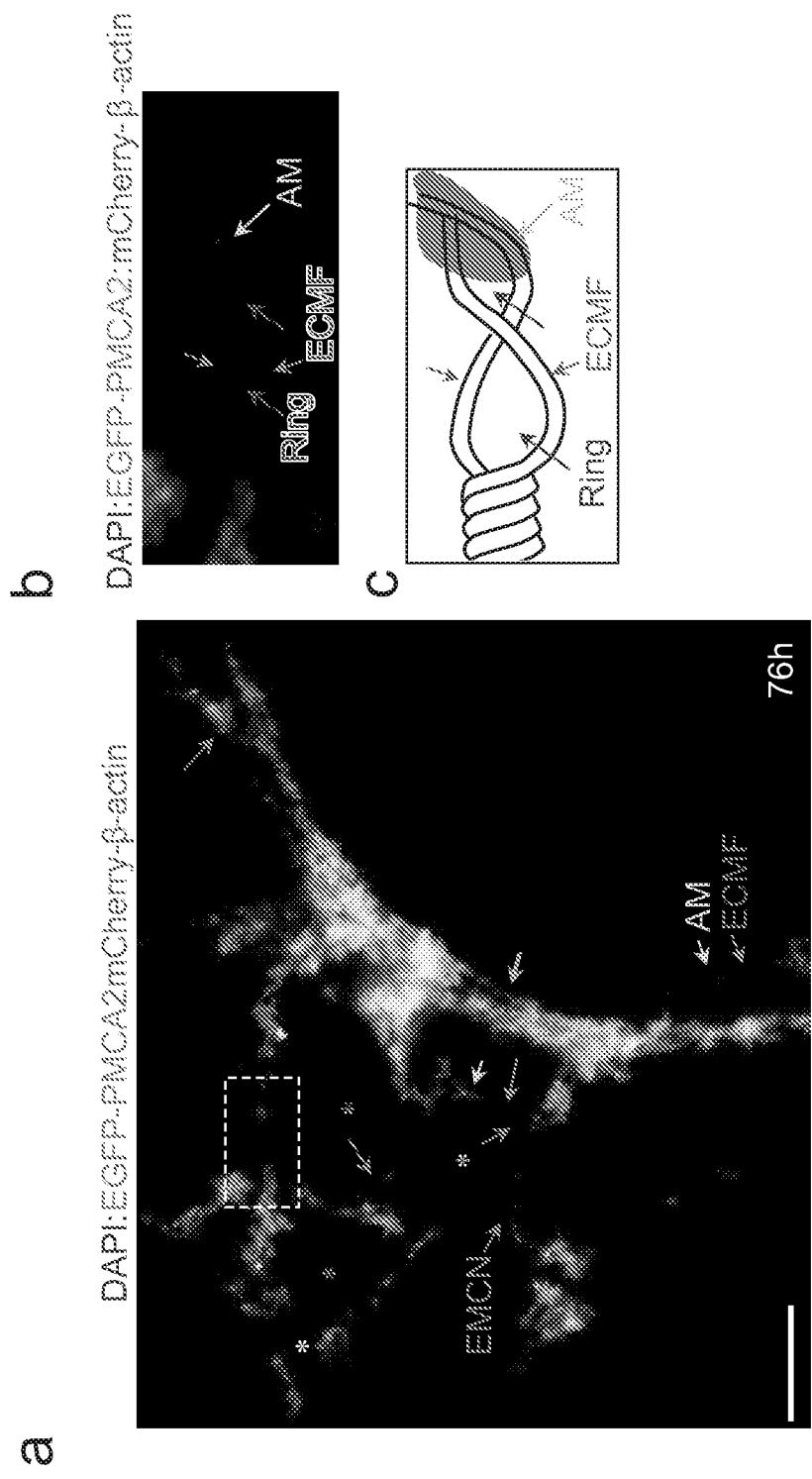
FIGS. 5A-C show images of the architectural structures of extracellular microfilament networks.

Aspects of the present disclosure are based on the heretofore undiscovered observation that native primary human epithelial cells grown in matrix support produce large-area microfilament networks. According to one aspect, the microfilament network can function as physical barriers for prevention and management of wound infection. Certain embodiments of the present disclosure are directed to a continuous network of cell-derived microfilaments as well as tissue engineering methods to produce large-area microfilament networks. The extracellular microfilaments formed under the conditions disclosed herein do not exist in multicellular organisms. Such microfilament networks have utilities in wound healing including, e.g., prevention of wound infection, including burn care, acute and surgical wound care. According to certain aspects, the microfilament networks promote cell migration and facilitate tissue regeneration. According to one aspect, normal primary human epithelial cells cultured on cell matrix generate a large-area of microfilament network. In one embodiment, the microfilament network is processed to remove the nuclei or DNA of the cells. In another embodiment, the microfilament network is physically, chemically and/or mechanically processed to remove the cells. According to another aspect, the microfilament network has utility in wound healing, e.g., as physical barrier and is applied to the wounds to prevent micro-organism induced wound infection. In certain embodiments, the bioengineering methods produce large-area (up to 500 cm$^2$) microfilament network. Such network is useful for wound infection prevention. In one embodiment, the network of cell-derived microfilaments is biodegradable and biologically compatible with the patient's tissue. In another embodiment, the microfilament network is capable of excluding micro-organisms from the wound site. In yet another embodiment, the microfilament network is semipermeable for constructing microenvironments that support the functions of the heterogeneous cells involved in tissue restoration and/or tissue regeneration. In one embodiment, the large-area of continuous network of cell-derived microfilaments overcomes one of the major obstacles in the treatment and healing of patients with large-area second (or third) degree thermal burn wounds.

According to one aspect, we a reliable method of generating ultra-large, porous, dense, multilayered and three dimensional (3D) extracellular microfilament meshes for facilitating wound repair is provided. It was found that human epithelial cell masses produce long, membrane-enclosed extracellular microfilaments (ECMFs). In one embodiment, nested ECMFs form superlarge extracellular microfilament networks (EMNs). In another embodiment, these EMNs connect and can form square foot (ft2)-scale ultra-large microfilament lattices (UMLs). In certain embodiments, these UMLs construct an environment for cell migration. In one embodiment, removing cell masses produces acellular UMLs (AUMLs) that can be used to facilitate wound repair. In an exemplary embodiment, when applied to second degree thermal burn wounds of mice, the AUMLs allow keratinocytes to engender large tunnels in the reepithelialzed epidermis, thus providing pathways for cells and nutrients to the site of wound repair. Properties of these large AUMLs include biodegradability, biocompatibility, and semipermeability. In certain embodiments, the AUMLs containing native biochemical, biophysical, and biomechanical components that are suitable for broad use in wound repair and tissue regeneration.

Microfilaments, the main cytoskeletal polymers in eukaryotic cells, are polymerized by actin subunits and actin-binding proteins. Microfilaments are essential for cell division and cytokinesis, cell shape maintenance, vesicle transportation, signal transduction, sensing, and cell motility (Gunning, P. W., Ghoshdastider, U., Whitaker, S., Popp, D. & Robinson, R. C. The evolution of compositionally and functionally distinct actin filaments. *Journal of cell science* 128, 2009-2019 (2015)). Cytoskeletal actin (including β- and γ-actin) assembly and depolymerization lead to microfilament network remodeling (Herman, I. M. Actin isoforms. *Current opinion in cell biology* 5, 48-55 (1993)). The μm-scale of adult animal cell sizes limits the potential area of the cytoskeletal microfilament network of single cells to the μm$^2$-scale (Lloyd, A. C. The regulation of cell size. *Cell* 154, 1194-1205 (2013), Ginzberg, M. B., Kafri, R. & Kirschner, M. Cell biology. On being the right (cell) size. *Science* 348, 1245075 (2015)). According to one aspect, human epithelial cell masses generate superlarge extracellular microfilament networks that facilitate cell migration. According to another aspect, the present disclosure provides a general strategy to engender artificial and ultra-large extracellular microfilament networks in the level of square foot (ft$^2$). According one aspect, human cell masses generate ultra-large (ft$^2$) scale mesh structures assembled by membrane-enclosed extracellular microfilaments. In one embodiment, these mesh structures are used by cells as functional ECM facilitating cell migration. According to another aspect, these native meshes are effective at promoting burn wound healing in mice. In certain embodiments, these meshes are simple, reliable, superlarge and 3D extracellular microfilament meshes (ft$^2$ or larger). In yet another embodiments, these meshes are porous, native, dense, or acellular. According to one aspect, these meshes could be used to facilitate wound repair and tissue regeneration. According to certain aspects, human epithelial cell masses generate long (up to 1000 μm in length) actin polymerized microfilaments extracellularly. According to one aspect, the microfilaments are membrane-enclosed. In one embodiment, the cell and the cell-derived extracellular microfilaments form superlarge continuous networks, which pave paths for cell migration. In another embodiment, decellularization engenders artificial, cell-less and superlarge (500 square centimeter, cm$^2$) lattices, increasing the microfilament network area up to about a billion-fold ($1 \times 10^9$-fold) in comparison to the cytoskeletal microfilament network area in a single human epithelial cell of the equivalent size. In a certain embodiment, the super-large and porous extracellular microfilament meshes facilitate the reepithelialzation and healing of the second degree thermal burn wounds in mice. According to certain aspects, the presently disclosed methods produce ultra-large scale extracellular microfilament networks that promote cell migration and are useful for tissue regeneration and wound healing.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

According to one aspect, the method of producing a network of microfilaments is via culturing cells in a matrix support and cell culture medium. In one embodiment, the cell masses form on top of the matrix support. In another embodiment, the matrix is the cell culture medium, Matrigel.

In one embodiment, the microfilaments of the network include actin, such as β-actin, γ-actin, and actin-interaction proteins. In one embodiment, the microfilaments are about 1-1000 µm, 10-900 µm, 20-800 µm, 30-700 µm, 40-600 µm, 50-500 µm, 60-400 µm, 70-300 µm, 80-200 µm, and 90-100 µm in length. In another embodiment, the microfilaments are branched. In yet another embodiment, the microfilaments have about 2-10, 3-9, 4-8, 5-7 branches. In one embodiment, the network further includes adhesive materials. In one embodiment, the adhesive materials associate with the microfilaments and enlarge the diameter of the microfilaments. In one embodiment, the network has an area in the range of about 1 µm$^2$ to about 500 cm$^2$. In another embodiment, the network has an area of about 10 µm$^2$ to about 400 cm$^2$, about 100 µm$^2$ to about 300 cm$^2$, about 200 µm$^2$ to about 200 cm$^2$, about 1000 µm$^2$ to about 100 cm$^2$ and about 1 cm$^2$ to about 10 cm$^2$. In another embodiment, the network has a thickness in the range of about 1 nm to about 1 cm, about 10 nm to about 0.1 cm, about 100 nm to about 0.01 cm and about 1000 nm to about 0.001 cm. In one embodiment, the network is applied to an area in need of treatment as a single layer. In another embodiment, multiple layers of the network can be applied to the area in need of treatment.

In certain embodiments, the pore size of the network ranges from about 0.1-5 µm, about 0.2-4 µm, about 0.3-3 µm, about 0.4-2 µm and about 0.1-1 µm in diameter. In one embodiment, the network can include bioactive and/or bioinactive agents. In some embodiments, the bioactive and/or bioinactive agents include integrins, adhesion receptors, and membrane proteins. In another embodiment, the bioactive agents are therapeutic drugs including antibodies and microorganism inhibitors. In one embodiment, the network is present on a matrix support. In certain embodiment, the matrix support is biodegradable. In an exemplary embodiment, the network is present on a Matrigel matrix support. In one embodiment, the microfilament source regions include eukaryotic cells with or without genetic modification.

According to another aspect, the present invention provides a method for treating a medical condition via applying the microfilament network of to an area in need of treatment. In some embodiments, the medical conditions relate to many types of wounds known to a skilled in the art, including but are limited to wounds, acute wounds and chronic wounds, burn wounds, thermal burn wound, chemical burn wounds, and electric burn wounds. In one embodiment, the microfilament network is applied with the matrix. In another embodiment, the method further includes separating the matrix substrate from the continuous extracellular microfilament network and the microfilament network is applied without the matrix.

Administration of agents and compositions described herein according to the various methods of the invention may be achieved according to a variety of methods. For example, the agents and compositions of the invention can be administered by any suitable means, e.g., parenteral, intravenous, subcutaneous, intramuscular, intraorbital, ophthalmic, intraventricular, intracranial, intracapsular, intraspinal, intracisternal, intraperitoneal, buccal, rectal, vaginal, intranasal or aerosol administration. Administration may be local, i.e., directed to a specific site, or systemic. Administration may also be effected by, but not limited to, direct surgical implantation, endoscopy, catheterization, or lavage. If applied during surgery, the compositions of the invention may be flowed onto the tissue, sprayed onto the tissue, painted onto the tissue, or any other means within the skill in the art. Alternatively, compositions of the invention applied during surgery may be incorporated into a suitable matrix. Further, compositions of the invention applied during surgery may be implanted in a patient at the site of a wound where re-epithelialization is desired.

The compositions of the invention may be administered in or with an appropriate carrier or bulking agent including, but not limited to, a biocompatible oil such as sesame oil, hyaluronic acid, cyclodextrins, lactose, raffinose, mannitol, carboxy methyl cellulose, thermo or chemo-responsive gels, sucrose acetate isobutyrate. As will be appreciated by those skilled in the art, the concentration of the drugs/compounds described in the compositions of the invention will vary depending upon a number of factors, including without limitation the dosage of the drug to be administered, the chemical characteristics (e.g., hydrophobicity) of the compounds employed, and the route of administration. The preferred dosage of drug to be administered also is likely to depend on variables including, but not limited to, the type and extent of a disease, tissue loss or defect, the overall health status of the particular patient, the relative biological efficacy of the compound selected, the formulation of the compound, the presence and types of excipients in the formulation, and the route of administration. The therapeutic molecules of the present invention may be provided to an individual where typical doses range from about 10 ng/kg to about 1 g/kg of body weight per day; with a preferred dose range being from about 0.1 mg/kg to 100 mg/kg of body weight, and with a more particularly preferred dosage range of 10-1000 µg/dose. The skilled clinician would appreciate that the effective doses of the present invention can be modified in light of numerous factors including, but not limited to, the indication, the pathology of the disease/wound, and the physical characteristics of the individual. It is also clearly within the skill in the art to vary, modify, or optimize doses in view of any or all of the aforementioned factors.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example I

Experimental Procedures

Cells, Culture Media, Plasmids, Reagents, and Mice.

Normal primary human mammary epithelial cells (HMECs, ATCC®PCS-600-010™) were ordered from ATCC. All cells used in this study were tested and found to be free of *mycoplasma* contamination. MEGM™ Mammary Epithelial Cell Growth Medium BulletKit™ (Clonetics™ MEGM™ Mammary Epithelial Cell Growth Medium plus SingleQuots™ Kit package) were ordered from Lonza (CC-3150). HMECs were cultured in MEGM BulletKit™ with/without the Matrigel matrix layers at 37° C. in humidified 5% $CO_2$ atmosphere. EGFP-hPMCA2z/b ($^\#$47584) and mCherry-β-actin ($^\#$54967) plasmids were ordered from Addgene. Anti-γ-Actin (gamma Actin, monoclonal, ab123034) and Anti-pan-Cadherin (polyclonal, ab140338) antibodies were ordered from Abcam. Matrigel™ Membrane Matrix (CB-40234) and Corning® Matrigel® Basement Membrane Matrix, Phenol Red-Free, *LDEV-Free (Product #356237) were purchased from Corning. Corning® 500 cm$^2$ Square TC-Treated Culture Dishes (Product #431110) were ordered from Corning. Mepiform® (a silicone membrane for wound care, Warner, P. M., Coffee, T. L. & Yowler, C. J. Outpatient burn management. *The Surgical clinics of North America* 94, 879-892 (2014).) was ordered from Mölnlycke Healthcare. The 6-week-old female mice (Strain name: BALB/cJ) were ordered from the Jackson Laboratory. Animal experiments were performed with the approval of the Institutional Animal Care and Use Committee of Harvard Medical School.

Extracellular Microfilament Development and Transient Transfection.

The Matrigel™ Membrane Matrix was thawed at 4° C. overnight. The Matrigel layers (20~30 µm in depth) were prepared in pre-chilled 6-well-plates, 10 cm dishes or 500 cm$^2$ square dishes, followed by gel for 20 minutes at 25° C. in humidified 5% $CO_2$ atmosphere. For the fluorescence imaging, the Matrigel layers were prepared with Phenol Red-Free Matrigel on the VWR-Micro covers in 6-well-plates. HMECs were plated on the Matrigel layers and cultured in the MEGM BulletKit™ media at 37° C. in a humidified atmosphere of 5% $CO_2$. The extracellular microfilaments were developed from 48-110 h after cell culture. Plasmids of EGFP-hPMCA2z/b (Addgene, #47584) and mCherry-β-actin (#54967) were transfected into HMECs using Lipofectamine® 2000 (Life Technologies, #11668027) according to the manual. Anti-γ-Actin (gamma Actin, monoclonal, ab123034) and Anti-pan-Cadherin (polyclonal, ab140338) antibodies were ordered from Abcam. Two days after transfection, the transfected cells were plated on the Matrigel matrix layers ($1 \times 10^3$ cells per well of 6-well-plate) in the indicated media. After a culturing period of the indicated time, the cells and Matrigel were fixed with 4% paraformaldehyde (PFA). Hematoxylin and eosin (H&E) staining of cells was performed after cell fixation. Samples with VWR-Micro covers were transferred onto glass slides followed by imaging acquisition.

Imaging Acquisition.

Phase contrast images were taken with a Nikon TMS inverted phase contrast microscope and a Nikon Coolpix auto 4300 digital camera. Fluorescence images of fixed cells were taken with an 80i upright microscope and a digital Hamamatsu ORCA-ER cooled CCD camera with a 20× or 40× lens and MetaMorph image acquisition software. Hematoxylin and eosin staining images of fixed cell or tissue sections were taken with 80i upright microscope and a digital Hamamatsu ORCA-ER cooled CCD camera with a 20× or 40× lens and NIS-Elements acquisition software.

Toluidine Blue Staining.

HMECs were plated atop the Matrigel matrix layers (about 60 µm in depth) on plastic discs in 6-well plates. HMECs were fixed using fixative mixtures of Formaldehyde-Glutaraldehyde-Picric-Acid Fixative (2.5% paraformaldehyde, 5.0% Glutaraldehyde, and 0.06% picric acid in 0.2M Cacodeylate buffer): cell culture media=1:1. The fixed HMECs were then postfixed for 30 min in 1% osmium tetroxide (OsO4)/1.5% potassiumferrocyanide ($KFeCN_6$), washed in water 3 times, and incubated in 1% aqueous uranyl acetate for 30 min. This was followed by 2 washes in water and dehydration a gradient of alcohol (5 min each; 50%, 70%, 95%, 2×100%) (Basler, M., Pilhofer, M., Henderson, G. P., Jensen, G. J. & Mekalanos, J. J. Type VI secretion requires a dynamic contractile phage tail-like structure. *Nature* 483, 182-186 (2012)). Cells were infiltrated for 2 h to overnight in a 1:1 mixture of propyleneoxide and TAAB Epon (Marivac Canada Inc. St. Laurent, Canada). The samples were subsequently embedded in TAAB Epon and polymerized at 60° C. for 48 h. Ultrathin sections (about 60 nm) were cut using a Reichert Ultracut-S microtome. The ultra-sectioned specimens were then stained with toluidine blue (for 30 seconds). Images were taken with an 80i upright microscope (20×, 40× lenses).

Decellularization.

After cell culturing (6×10$^4$ HMECs on the Matrigel layers in the 500 cm$^2$ dishes) for the indicated duration, HMECs and ultra-large scale extracellular microfilament networks in the 500 cm$^2$ dishes (Corning® 500 cm$^2$ Square TC-Treated Culture Dishes) were fixed with 4% paraformaldehyde for 10 min, followed by 3 washes with 1×PBS and H&E staining. The cell masses and cells were removed with pipette tips (1 mL or 100 µL) and a Nikon TMS inverted phase contrast microscope followed by three washes with 1×PBS. After cell culturing for the indicated time, cells and superlarge extracellular microfilament networks were fixed with 0.5% KMnO4 (in 1×PBS, pH 7.1, for lipid stabilization, Zhao, S. et al. Fixation-induced cell blebbing on spread cells inversely correlates with phosphatidylinositol 4,5-bisphosphate level in the plasma membrane. FEBS Open Bio 4, 190-199 (2014).) for 1 h, followed by 10% neutral buffered formalin fixative for 15 min. Then, three washes with 1×PBS were performed to remove free chemical residue. The cell masses and cells were removed with pipette tips (1 mL or 100 µL) and a Nikon TMS inverted phase contrast microscope followed by three washes with 1×PBS to remove the detached cells. The AUMLs were tailored and separated from the Matrigel matrix. The AUMLs without Matrigel were transferred onto the wound surfaces with the top side of the AUML layer contact with the wound surface by self-made AUML specific transferring devices for thermal burn wound healing analyses.

Animal Thermal Burn Wound Healing Assay.

The 6-week-old adult BALB/cJ female mice were weighed (weight, 20~24 g) and anesthetized with 10 mg/kg xylazine (AnaSed® Injection, Xylazine Sterile Solution) by intraperitoneal (IP) injection. The hair was clipped from the backs of the anesthetized mice, and the area was denuded with a commercially available hair remover. The deep second degree thermal burn wounds (with a diameter of 1.5 cm) were induced into 15 mice by exposing the skin to 98° C. steam for 4 seconds (Zhang, Y. et al. Role for heat shock protein 90alpha in the proliferation and migration of HaCaT cells and in the deep second-degree burn wound healing in mice. *PLoS One* 9, e103723 (2014)). The 15 mice with deep second degree thermal burn wounds were randomly divided into three groups (5 mice per group). The wounds were managed with/without treatment of Mepiform® or tailored AUMLs every other day. Images of the wounds were taken by a Nikon camera. At 14 d (day) post-burn, the mice were sacrificed and the wounds were excised for histological evaluation via H&E staining analyses (sectioned specimen, 5 µm in depth).

Double Immunohistostaining Analyses.

The cutaneous wounds were excised, fixed with Histo-Choice® MB fixative (Amresco), and embedded in paraffin. The sectioned specimens (5 µm in depth) were subjected to double immunohistochemistry staining with anti-pan-Cadherin antibodies (Abcam, ab140338, 1:200; Life Technologies, #982425, Alex Fluor®488 goat anti-rabbit IgG (H+L) secondary antibody, 1:1000), anti-γ-actin antibodies (Abcam, ab123034, 1:200; Life Technologies, Alex Fluor®568 goat anti-rabbit IgG (H+L) secondary antibody, 1:1000), and 4',6-diamidino-2-phenylindole (DAPI, 1:1000). Fluorescence images were taken with a Nikon 80i upright microscope with a 20×/40×/60× lens. All images were obtained using MetaMorph image acquisition software.

Statistical Analyses.

Statistical analyses were performed as previously described (Yi, T. et al. eIF1A augments Ago2-mediated Dicer-independent miRNA biogenesis and RNA interference. *Nat Commun* 6, 7194 (2015).). Data (error bars) are presented as the mean and SD (n=3 or more). P-value was determined using the Student's t-test (tail=2). , P<0.01; *, P<0.001.

Normal primary human mammary epithelial cells (HMECs) were plated on an indicated thick (3D) Matrigel matrix-culture media mixture gel layer. In contrast to 2D culture, the individual HMECs did not exhibit irregular shapes, but consistently presented a spherical morphology, with a minimal surface area remaining in contact with the Matrigel (FIGS. 1A-B). This indicates that the Matrigel is an unfavorable environment for cell adhesion, attachment and spreading. At longer times, however, the HMECs migrated, aggregated, proliferated, and formed compact cell masses with multiple stacked cells maintaining no contact with the Matrigel matrix (FIGS. 1C-D). There is no cell-generated substance surrounding the cell masses at 24 or 36 hours (h) after cell implantation (FIGS. 1C-D). However, upon hematoxylin and eosin (H&E) staining imaging, we found that at 102 h after implantation, the cell masses had generated superlarge mesh structures external to and surrounding the cell masses, and covering the whole Matrigel surfaces in wells (6-well-plate) or 10 cm dishes (FIGS. 1E-F).

To investigate whether the superlarge mesh is constructed by membrane-enclosed units, membrane-associated molecular markers were detected. Plasma membrane calcium-transporting ATPase-2 (PMCA2) functions as a calcium extrusion pump that removes Ca$^{2+}$ from cells (See, Street, V. A., McKee-Johnson, J. W., Fonseca, R. C., Tempel, B. L. & Noben-Trauth, K. Mutations in a plasma membrane Ca2+-ATPase gene cause deafness in deafwaddler mice. *Nature genetics* 19, 390-394 (1998)) and regulates the Ca$^{2+}$ content of a number of cell types, including mammary epithelial cells (See, VanHouten, J. et al. PMCA2 regulates apoptosis during mammary gland involution and predicts outcome in breast cancer. *Proceedings of the National Academy of Sciences of the United States of America* 107, 11405-11410 (2010)). Thus, HMECs were transiently co-transfected with plasmids encoding enhanced green fluorescence protein (EGFP)-tagged PMCA2 (EGFP-PMCA2). Upon fluorescence imaging, EGFP-PMCA2 was found to be distributed throughout the plasma membranes of cells and along the surfaces of a large portion of the nested microfibers surrounding the cell masses. This suggests that the cell masses vigorously produce large quantities of membrane-enclosed extracellular microfibers (FIG. 2A) that connect the cell masses. The long and short extracellular microfibers densely connect and thus constitute a continuous network (FIG. 2A).

The two non-muscle and highly conserved isoactins, β- and γ-actin, are both microfilament components and play multiple roles in cytokinesis (See, Pollard, T. D. et al. Actin and myosin biochemistry in relation to cytokinesis. *Annals of the New York Academy of Sciences* 582, 120-130 (1990)), organelle transportation (See, Bretscher, M. S. Getting membrane flow and the cytoskeleton to cooperate in moving cells. *Cell* 87, 601-606 (1996)), signal transduction (See, Janmey, P. A. The cytoskeleton and cell signaling: component localization and mechanical coupling. *Physiological reviews* 78, 763-781 (1998)), cell mobility (See, Theriot, J. A. & Mitchison, T. J. Actin microfilament dynamics in locomoting cells. *Nature* 352, 126-131 (1991); Mitchison, T. J. & Cramer, L. P. Actin-based cell motility and cell locomotion. *Cell* 84, 371-379 (1996); Pollard, T. D. & Borisy, G.

G. Cellular motility driven by assembly and disassembly of actin filaments. *Cell* 112, 453-465 (2003)), and the maintenance and alteration of cell shapes (See, Gardel, M. L. et al. Elastic behavior of cross-linked and bundled actin networks. *Science* 304, 1301-1305 (2004); Herman, I. M. Actin isoforms. *Current opinion in cell biology* 5, 48-55 (1993); Keren, K. et al. Mechanism of shape determination in motile cells. *Nature* 453, 475-480 (2008)). In addition, it was investigated whether β-actin is involved in the composition of extracellular microfibers. Two plasmids encoding mCherry-tagged-β-actin (mCherry-β-actin) and EGFP-PMCA2 were transiently co-transfected into HMECs, after which the β-actin was found to be distributed throughout the cytoplasm and along all extracellular microfibers (FIG. 2B). This demonstrates that the microfilaments are structural components of the membrane-enclosed extracellular microfibers (FIGS. 2A-B). The nested extracellular microfilaments form networks via microfilament connection nodes, leaving variable sizes of large multilateral space between them (FIG. 2B). The porous (multilateral pores), extracellular microfilament assembled networks then connect, forming a superlarge, continuous, porous extracellular microfilament network surrounding the cell masses (FIGS. 2A-B). The extracellular microfilaments possess potent ability for branching morphogenesis (FIGS. 2A-B and FIG. 3). The number of extracellular microfilaments increased rapidly, forming dense networks quickly (FIG. 4A-E). The above data suggests that these superlarge meshes of persistent, long, highly branched, membrane-enclosed extracellular microfilaments, which do not exist in multicellular organisms to our current knowledge, are created here for the first time. These previously unappreciated structures have a high capacity for network formation and differ from cytoskeletal microfilaments and stress fibers (See, Tojkander, S., Gateva, G. & Lappalainen, P. Actin stress fibers—assembly, dynamics and biological roles. *Journal of cell science* 125, 1855-1864 (2012)), basement membranes (See, Nelson, D. A. & Larsen, M. Heterotypic control of basement membrane dynamics during branching morphogenesis. *Developmental biology* 401, 103-109 (2015)), un-branched epithelial bridges (See, Zani, B. G., Indolfi, L. & Edelman, E. R. Tubular bridges for bronchial epithelial cell migration and communication. *PloS one* 5, e8930 (2010)), or short and/or transient filopodia (See, Mattila, P. K. & Lappalainen, P. Filopodia: molecular architecture and cellular functions. *Nature reviews. Molecular cell biology* 9, 446-454 (2008)), cilia, microvilli (See, Cutz, E. et al. Microvillus inclusion disease: an inherited defect of brush-border assembly and differentiation. *The New England journal of medicine* 320, 646-651 (1989)), podosomes, and invadopodia (See, Murphy, D. A. & Courtneidge, S. A. The 'ins' and 'outs' of podosomes and invadopodia: characteristics, formation and function. *Nature reviews. Molecular cell biology* 12, 413-426 (2011)).

Multiple long extracellular microfilaments align together to form thick bundles. Two or more extracellular microfilaments can twist together to create twisted bundles with rings (FIGS. 2B and 5A-C). These observations indicate that the architectural structures of the organized extracellular microfilament networks (EMSs) are highly diverse. The above results demonstrate that one of the primary properties of HMEC cell masses is their production of extracellular membrane-enclosed microfilaments, via which they robustly create superlarge, continuous, and porous EMNs (FIGS. 2A-B and 4A-E to 5A-C).

Figure 6:
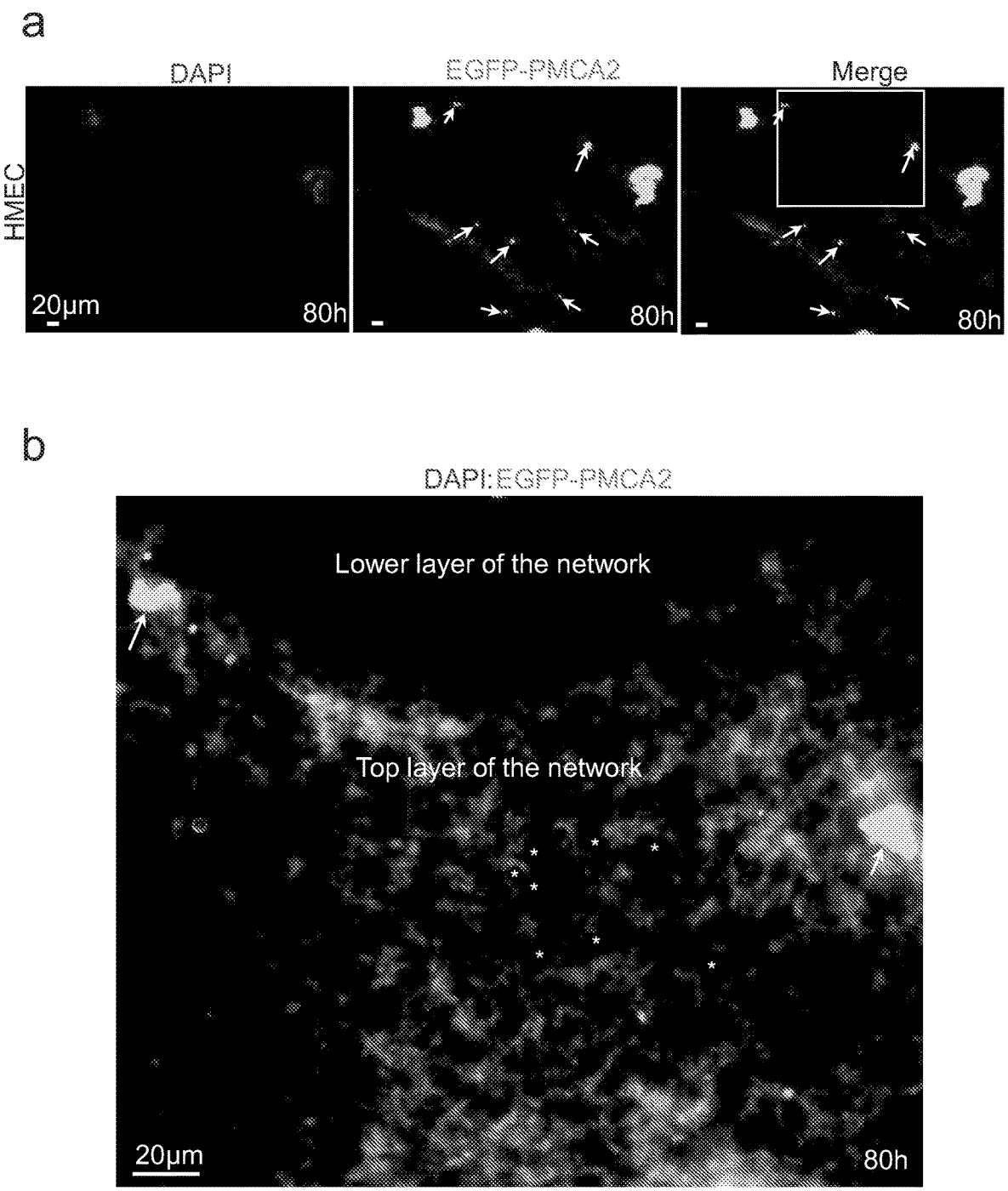
FIGS. 6A-B show fluorescent images of extracellular microfilaments forming superlarge, porus, multilayered and dense networks.

Over time (80 h), multiple EMN complexes connect and combine into a superlarge, continuous, porous, multi-layered lattice surrounding the cell masses, and spread across the Matrigel surfaces (FIG. 6A-B). There are unidentified membrane-enclosed round dots in varying sizes scattered throughout these superlarge 3D EMNs (FIG. 6A-B).

Figure 7:
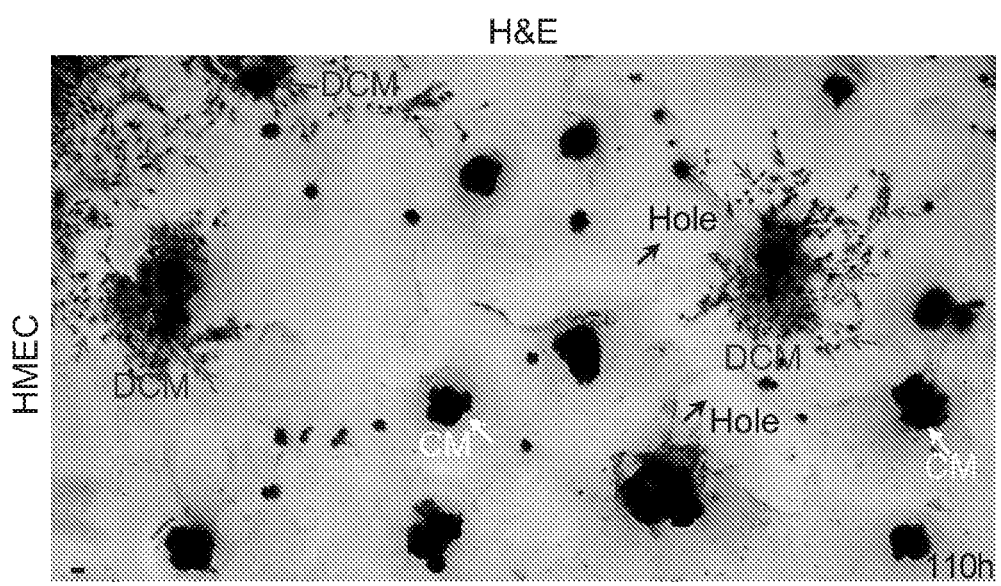
FIG. 7 shows an image of cells migrating on the surfaces of the superlarge extracellular microfilament meshes. HMECs were transplanted onto the Matrigel matrix surface and cultivated for 110 h. H&E image shows that several HMEC cell masses are disassembled (blue arrows; DCM, disassembled cell masses). The individual cells (indicated by red arrows), which have detached, migrated, and left the cell mass sites, migrate on the surfaces of the superlarge extracellular microfilament network (but not in the large hole where the Matrigel surface is exposed). These mobile cells are of variable morphologies but none possess the sphere morphology. White arrows: non-disassembled cell masses. Scale bar=10 µm.

To identify the potential functions of these superlarge EMNs, HMECs were continuously cultured for 110 h after the implantation of cells on the Matrigel layers. At 110 h, the cell masses began to disassemble, and the individual cells detached, migrated, left the cell mass sites, and either remained on or traveled along the surfaces of the superlarge EMN, avoiding the Matrigel surfaces in the large round holes which are caused by the disassembly of EMNs (FIG. 7). In addition, the individual cells originating from the disassembled cell masses possessed irregular morphologies, with no spherical cells being observed (FIG. 7). These results indicate that the surfaces of the superlarge EMNs facilitate cell adhesion, attachment, spreading, migration and other behavior. Taken together, the above data demonstrated that the cell masses generate superlarge continuous EMNs to create environments favorable for cellular activity, and pave new avenues for cell migration (FIGS. 1A-F, 2A-B, 3, 4A-E, 5A-C, 6A-B and 7).

To examine whether the cell masses can effectively develop $ft^2$-scale EMNs, we implanted HMECs on the Matrigel layer of 500 $cm^2$ culture plates. The cell masses generated ultra-large EMNs that covered the entire 500 $cm^2$ Matrigel surface (FIGS. 8A-B), demonstrating the cell masses' extraordinary capacity to produce ultra-large scale EMNs, which suggested potential applications for wound healing if the cells are removed. The removal of xenogeneic and allogeneic cellular genetic materials via decellularization results in the production of minimally immunogenic native structures for use in tissue regeneration[26]. To achieve this, after fixation the cell masses and cells were removed, to produce artificial 500 $cm^2$ ($ft^2$-level) ultra-large and cell-less extracellular microfilament meshes (FIG. 8C). These data indicate that the potential size of these acellular ultra-large scale extracellular microfilament lattices (AUMLs) isn't limited by any of the structure's inherent characteristics.

It is estimated that over 6.6 million people worldwide suffer from various burns every year, and the annual number of global fatal burns has increased from 280,000 in 1990 to 338,000 in 2010 (Lozano, R. et al. Global and regional mortality from 235 causes of death for 20 age groups in 1990 and 2010: a systematic analysis for the Global Burden of Disease Study 2010. *Lancet* 380, 2095-2128 (2012)). Re-epithelialization and wound healing is a challenge for patients with large-area second (or third) degree thermal burn wounds. One of the major obstacles to treatment and healing is the absence of large-area continuous materials with the required characteristics: the material must be degradable, biologically compatible with the patient's tissue, capable of excluding micro-organisms from the wound site, and semipermeable in order to construct microenvironments (See, Heng, M. C. Wound healing in adult skin; aiming for perfect regeneration. *International journal of dermatology* 50, 1058-1066 (2011)) that support the functions of the heterogeneous cells (See, Taylor, G., Lehrer, M. S., Jensen, P. J., Sun, T. T. & Lavker, R. M. Involvement of follicular stem cells in forming not only the follicle but also the epidermis. *Cell* 102, 451-461 (2000); Watt, F. M., Lo Celso, C. & Silva-Vargas, V. Epidermal stem cells: an update. *Current opinion in genetics & development* 16, 518-524 (2006); Watt, F. M. & Jensen, K. B. Epidermal stem cell diversity and quiescence. *EMBO molecular medicine* 1, 260-267(2009)) involved in tissue restoration (See, Braun, K. M. & Prowse, D. M. Distinct epidermal stem cell compartments are maintained by independent niche microenvironments. *Stem cell reviews* 2, 221-231(2006); Solanas, G. & Benitah, S. A. Regenerating the skin: a task for the heterogeneous stem cell pool and surrounding niche. *Nature reviews. Molecular cell biology* 14, 737-748 (2013); Nowak, J. A., Polak, L., Pasolli, H. A. & Fuchs, E. Hair follicle stem cells are specified and function in early skin morphogenesis. *Cell stem cell* 3, 33-43 (2008)).

To investigate whether the superlarge, continuous, porous, multilayered and native AUMLs can create environments that facilitate the healing of burn wounds, second degree thermal cutaneous burn wounds were performed in mice with/without treatment of Mapiform (Warner, P. M., Coffee, T. L. & Yowler, C. J. Outpatient burn management. *The Surgical clinics of North America* 94, 879-892 (2014)), or AUMLs. At 14 d post-burn, the AUML was found to have more effectively promoted the re-epithelialization and healing of the second degree thermal burn wounds than either lack of treatment or treatment with Mepiform (FIG. 9A and FIG. 10A).

While epidermis is avascular the dermis supplies the avascular epidermis with nutrients via its vascular network (Reinke, J. M. & Sorg, H. Wound repair and regeneration. European surgical research. Europaische chirurgische Forschung. Recherches chirurgicales europeennes 49, 35-43 (2012), Yamaguchi, Y. & Yoshikawa, K. Cutaneous wound healing: an update. The Journal of dermatology 28, 521-534 (2001)). Cadherins are transmembrane proteins that perform a vast array of functions, including keratinocyte adhesion and migration (Lecuit, T. & Yap, A. S. E-cadherin junctions as active mechanical integrators in tissue dynamics. Nature cell biology 17, 533-539 (2015)). Interestingly, it was found that AUML treatment significantly promotes the generation of many large tunnels within the reepithelialized epidermis (FIGS. 9B-C and FIG. 10B, FIG. 12A and FIG. 13A). Histochemical and immunohistochemistry staining analyses demonstrated that these keratinocyte tunnels contain many different types of cells, including red blood cells, suggesting that these keratinocyte tunnels functionally provide pathways for cells, soluble growth factors and nutrients (FIG. 9B and FIGS. 11A-C, 12A-C and 13A-C). More importantly, it was found that keratinocytes generates EMNs in the keratinocyte tunnel lumens and diverse cells (including red blood cells) migrate in the keratinocyte EMNs, demonstrating that keratinocytes engender EMNs in vivo providing scaffolds for cell migration and other behavior (FIG. 9D and FIGS. 11A-C, 12A-C and 13A-C and 14A-C). Keratinocyte EMNs disassembled and cells filled the keratinocyte tunnels, which coincides the facts that keratinocyte tunnels and EMNs disappeared in the reepithelialized epidermis at the later stage, suggesting that AUMLs create appropriate environments for the orchestrated generation and decomposition of keratinocyte tunnels and EMNs (FIG. 9D, FIG. 10B and FIGS. 11A-C, 12A-C and 13A-C and 14A-C). Taken together, these data demonstrated that AUMLs built appropriate environments allowing keratinocytes to generate large keratinocyte tunnels that act as pathways for cells, soluble growth factors and nutrients, and engender large keratinocyte EMNs in vivo supplying scaffolds for cell migration and other behavior, thus facilitating wound repair.

The $ft^2$-scale AUMLs, which are completely generated by human cells, naturally employed by cells as scaffolds and environments for cell migration and other behavior, decellularized while keeping the native biophysical, biochemical, and biomechanical signals intact, enabled the application of AUMLs for the facilitation of wound repair. The characteristics of cell membrane-enclosed extracellular microfilaments allow the AUMLs to be used as biodegradable, biocompatible, semipermeable, and minimal immunogenic biomaterials for the facilitation of wound repair and tissue regeneration. The potential for creating very large area-AUMLs allows them to be easily tailored to wounds of any size. AUMLs promote the generation of large keratinocyte tunnels providing pathways for cells and nutrients, and the production of keratinocyte EMNs supplying scaffolds for cell migration and behavior in vivo. In this manner, the keratinocyte tunnels and EMNs fulfill the high demand for cells, soluble growth factors and nutrients in areas of the epidermis where cell migration, proliferation, differentiation and stratification are taking place as during tissue repair.

It is anticipated that these biodegradable, biocompatible, semipermeable and infinite AUMLs with their native biophysical, biochemical, and biomechanical signals will be applied as a method of treating a broad spectrum of wounds and facilitating tissue regeneration, as large-area native meshes facilitate cue-guided cell migration, proliferation and differentiation in developing highly organized tissues.

Data provided herein show that a previously unrecognized extracellular microfilament network, produced from cells grown in Matrigel, facilitates cell migration. The present disclosure contemplates cell-less and ultra-large scale ($ft^2$ scale) extracellular microfilament networks that facilitate the re-epithelialization and healing of second-degree thermal burn wounds.

Example II

Described are novel tissue engineering methods that produce large-area native primary normal human cell membranes for prevention and management of wound infection, including burn care, acute and surgical wound care. Normal primary human epithelial cells cultured on cell matrix generate a large-area (up to 500 $cm^2$) of primary normal human cell membrane without nuclei or DNA, which can be applied to the wounds and acts as physical barriers to prevent micro-organism induced wound infection. The engineered large area cell membrane-matrix complex layer can effectively prevent infection by micro-organisms, including bacteria, fungi and viruses.

Materials and Methods

Growth of Large Primary Normal Human Cell Membranes.

Matrigel™ matrix layers (Yi, T., Kabha, E., Papadopoulos, E., and Wagner, G. (2014) 4EGI-1 targets breast cancer stem cells by selective inhibition of translation that persists in CSC maintenance, proliferation and metastasis. *Oncotarget* 5, 6028-6037) in dishes with various sizes (75 $cm^2$, or 300 $cm^2$, or 500 $cm^2$, or more) were prepared on thin plastic membrane with Matrigel™ Membrane Matrix (CB-40234, Corning) and pre-chilled dishes followed by incubation in incubator at 37° C. for 20 minutes. Primary normal human mammary epithelial cells (HMECs) (Scheel, C., Eaton, E. N., Li, S. H., Chaffer, C. L., Reinhardt, F., Kah, K. J., Bell, G., Guo, W., Rubin, J., Richardson, A. L., and Weinberg, R. A. (2011) Paracrine and autocrine signals induce and maintain mesenchymal and stem cell states in the breast. *Cell* 145, 926-940) were cultured on Matrigel matrix layers in the DMEM media. The mammalian cells were cultured at 37° C. with 5% $CO_2$. After 50 hours culture, HMECs form cell masses and large area primary normal human cell membrane. Cell masses were removed by tips and large area primary normal human cell membranes without genetic materials of nucleus were generated. After DMEM media were removed, cell membranes were washed three time of 1×PBS.

Results

The large area native primary normal human cell membranes generated by this method (FIGS. 15A-B) have the characteristics including: 1) native cell membranes without nucleus with super-large area (up to 500 cm$^2$ or more); increase billion-fold ($10^{10}$-fold) in area compare to a single cell area; 2) double native primary normal human cell membrane layers; 3) no genetic materials of DNAs; 4) native lipid membrane with native membrane proteins; 5) easy degradation of cell membrane and Matrigel matrix; and 6) wound infection prevention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A network comprising extracellular microfilaments interconnected in a continuous lattice or mesh structure between a plurality of microfilament source regions, wherein the microfilament source regions comprise in vitro cultured cells, wherein the microfilaments comprise actin and are produced via culturing the cells on top of a 3D matrix support, wherein the cells are primary normal human mammary epithelial cells (HMECs), wherein HMECs proliferate and form aggregated cell masses, wherein the cell masses produce long, branched, and extracellular membrane-enclosed microfilaments that connect the cell masses, wherein the network has an area in the range of about 1 µm$^2$ to about 500 cm$^2$ and a thickness in the range of about 1 nm to about 0.5 cm, and wherein the 3D matrix is a gelatinous protein mixture.

2. The network of claim 1, wherein the actin comprises β-actin.

3. The network of claim 1, wherein the microfilaments are about 1-1000 µm in length.

4. The network of claim 1, wherein the microfilaments have about 2-10 branches.

5. The network of claim 1, wherein multiple microfilaments align together and form bundles of diverse architectural structures.

6. The network of claim 1, wherein the microfilament source regions form connection nodes for the continuous lattice or mesh structure.

7. The network of claim 1, wherein the network further comprises adhesive materials.

8. The network of claim 7, wherein the adhesive materials associate with the microfilaments and enlarge the diameter of the microfilaments.

9. The network of claim 1, wherein the network is single or multiple layered.

10. The network of claim 1, wherein the microfilaments comprise a surface area which is greater than an equivalent unit of an intra-cellular cytoskeletal microfilament network surface area.

11. The network of claim 1, wherein the network is porous having pore sizes ranging from about 0.1-5 µm in diameter.

12. The network of claim 1, wherein the network further comprises bioactive and bioinactive agents.

13. The network of claim 12, wherein the bioactive agents are therapeutic drugs.

14. The network of claim 1, wherein the 3D matrix support is biodegradable.

15. The network of claim 1, wherein the network is further processed to remove cells or nuclei from cells.

16. The network of claim 1, wherein the HMECs comprise genetic modifications.

17. The network of claim 1, wherein the 3D matrix support inhibits cell attachment and migration.

* * * * *